United States Patent [19]

Hahn et al.

[11] Patent Number: 5,893,515

[45] Date of Patent: *Apr. 13, 1999

[54] MIST GENERATOR

[75] Inventors: Gary S. Hahn, 2371 Lagoon View Dr., Cardiff By The Sea, Calif. 92007; David R. Williams, Temecula, Calif.

[73] Assignee: Gary S. Hahn, Cardiff By The Sea, Calif., CA

[*] Notice: This patent is subject to a terminal disclaimer.

[21] Appl. No.: 08/222,257

[22] Filed: Apr. 1, 1994

Related U.S. Application Data

[63] Continuation-in-part of application No. 07/974,801, Nov. 12, 1992, Pat. No. 5,346,132.

[51] Int. Cl.$^6$ .............................. B05B 3/08; B05B 11/02
[52] U.S. Cl. .................... 239/7; 239/215; 239/216; 239/223; 239/333; 239/289
[58] Field of Search .................... 239/71, 72, 214.25, 239/215, 219, 221, 222, 223, 289, 323, 331, 333, 338, 350, 354, 216; 222/113, 207, 325, 333; 604/289, 294, 296, 300

[56] References Cited

U.S. PATENT DOCUMENTS

| | | | |
|---|---|---|---|
| 2,607,571 | 8/1952 | Hession, Jr. | 239/215 X |
| 2,629,516 | 2/1953 | Badham . | |
| 2,749,179 | 6/1956 | Almquist | 239/222 X |
| 2,772,817 | 12/1956 | Jauch | 222/207 X |
| 2,826,194 | 3/1958 | Golden . | |
| 3,108,147 | 10/1963 | Flury | 239/216 X |
| 3,170,462 | 2/1965 | Hall . | |
| 3,181,796 | 5/1965 | Keller | 239/222 X |
| 3,188,007 | 6/1965 | Myklebust | 239/215 |
| 3,267,701 | 8/1966 | Mandarino | 239/215 X |
| 3,640,274 | 2/1972 | Costello . | |
| 3,716,170 | 2/1973 | Mangels . | |
| 3,784,804 | 1/1974 | Sabatelli et al. | 239/289 X |
| 3,812,853 | 5/1974 | Crain | 239/219 X |
| 4,135,647 | 1/1979 | Mascia et al. | 222/325 X |
| 4,154,375 | 5/1979 | Bippus | 222/325 |
| 4,162,037 | 7/1979 | Koyama | 222/333 X |
| 4,175,704 | 11/1979 | Cohen | 239/333 X |
| 4,294,407 | 10/1981 | Reichl et al. . | |
| 4,452,239 | 6/1984 | Malem . | |
| 4,515,294 | 5/1985 | Udall | 222/207 X |
| 4,515,295 | 5/1985 | Dougherty . | |
| 4,550,866 | 11/1985 | Moore | 604/294 X |
| 4,616,783 | 10/1986 | Weber et al. . | |
| 4,629,456 | 12/1986 | Edwards | 604/294 X |
| 4,641,384 | 2/1987 | Landsberger et al. . | |
| 4,758,237 | 7/1988 | Sacks . | |
| 4,784,652 | 11/1988 | Wikstrom . | |
| 4,793,339 | 12/1988 | Matsumoto et al. . | |
| 4,993,594 | 2/1991 | Becker et al. | 239/323 X |
| 5,020,526 | 6/1991 | Epstein . | |
| 5,022,587 | 6/1991 | Hochstein | 239/338 X |
| 5,046,665 | 9/1991 | Kor et al. | 239/71 |
| 5,053,000 | 10/1991 | Booth et al. . | |
| 5,152,435 | 10/1992 | Stand et al. | 239/333 X |
| 5,203,506 | 4/1993 | Gross et al. | 239/223 X |
| 5,248,096 | 9/1993 | Hoey et al. | 604/296 X |
| 5,346,132 | 9/1994 | Hahn et al. | 239/215 X |

FOREIGN PATENT DOCUMENTS

| | | | |
|---|---|---|---|
| 551853 | 1/1958 | Canada | 239/216 |
| 6607954 | 12/1967 | Netherlands | 239/216 |
| 192323 | 8/1937 | Switzerland | 239/215 |

OTHER PUBLICATIONS

Sunbeam–Northern Company Cool Spary Humidifier Instruction Book and photographs.
AOA News, Sept. 1, 1991, page 15 "Easy eyedrop dispenser available throiugh dispomed".
Eye Spa Advertisement.

*Primary Examiner*—Andres Kashnikow
*Attorney, Agent, or Firm*—Lyon & Lyon

[57] ABSTRACT

A device for generating a spray of mist or fine droplets includes a spinning rotor within a mist chamber. The rotor has inner walls which taper conically outwardly from the open bottom of the rotor to a hole near the top of the rotor. Liquid is pumped by a finger actuated pump from a cartridge module into a bowl surrounding the bottom end of the rotor. A spray is created as the liquid is formed into droplets as it passes through the hole in the rotor under centrifugal force. A directional light source is used for aiming the spray.

27 Claims, 32 Drawing Sheets

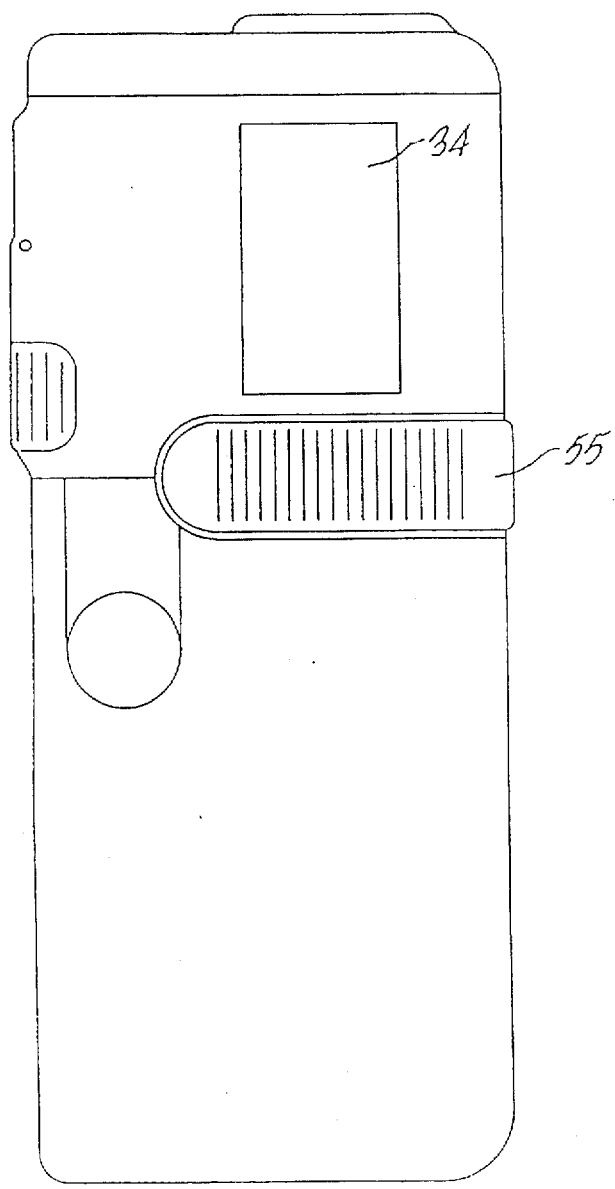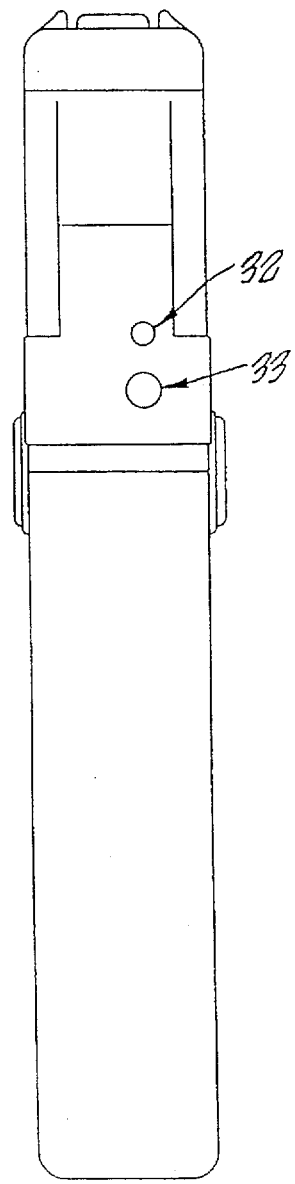
FIG. 5
FIG. 6

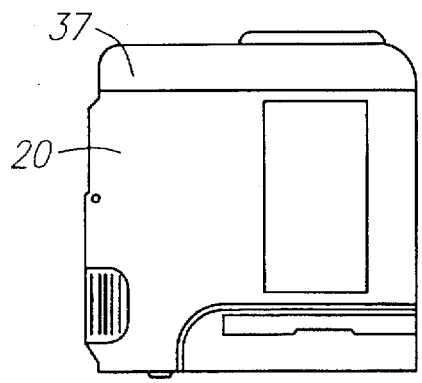
FIG. 18B          FIG. 19B
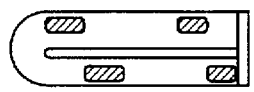
FIG. 18C
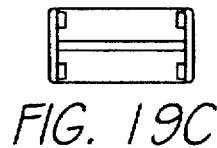
FIG. 19C
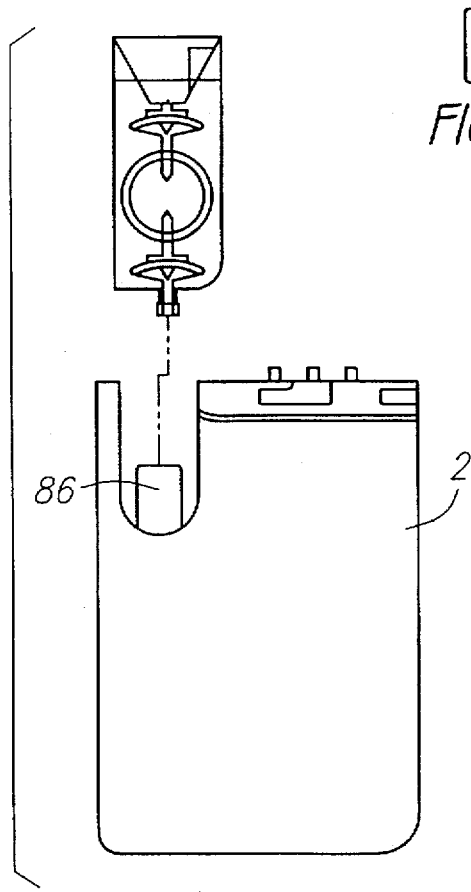
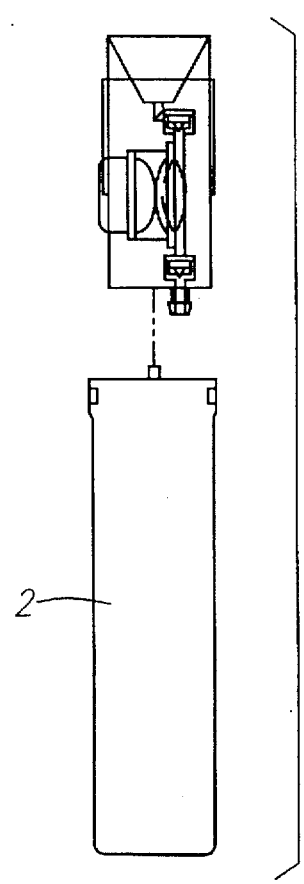
FIG. 18A          FIG. 19A

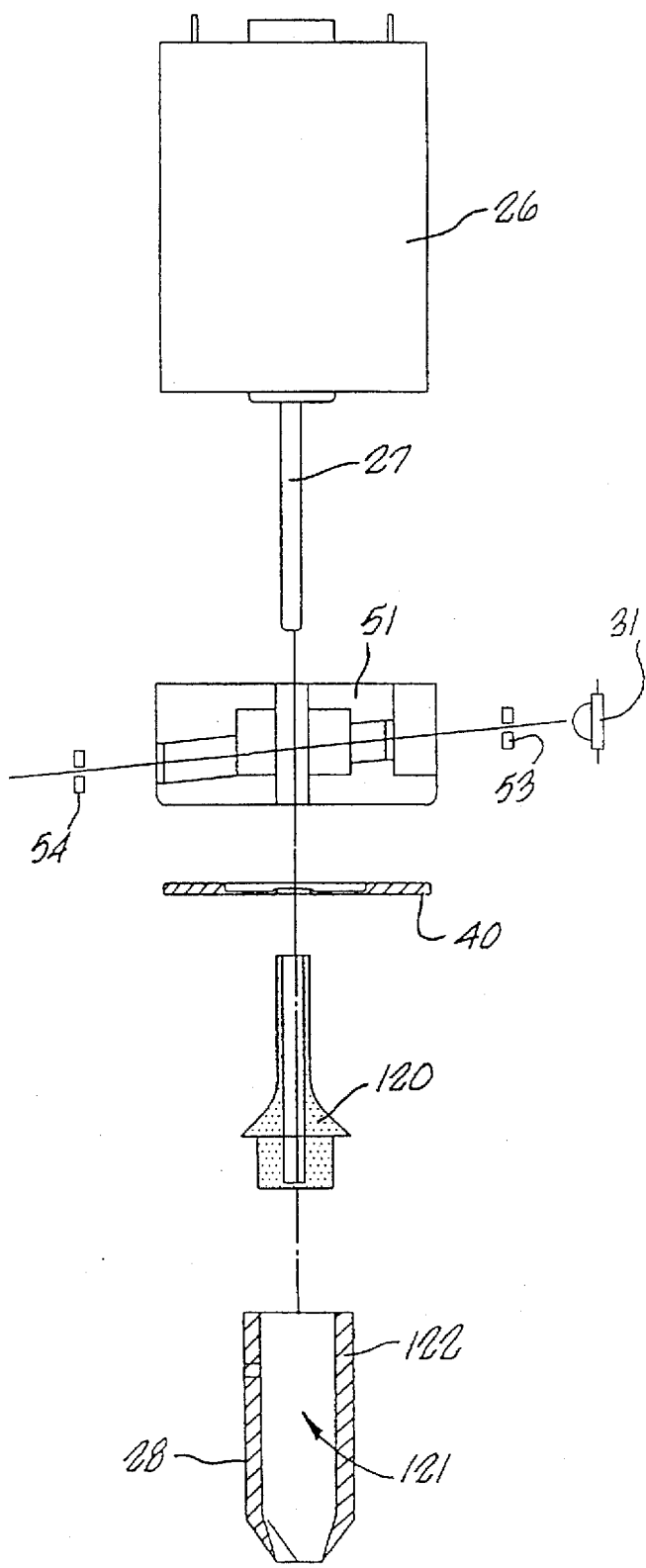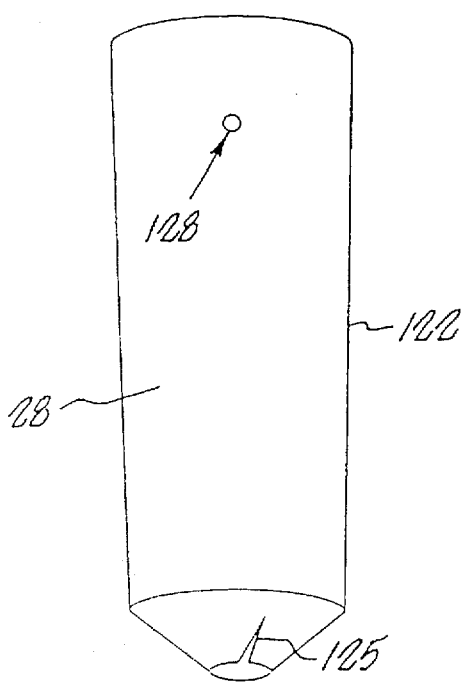
FIG. 32.
FIG. 33.

FIG. 47.
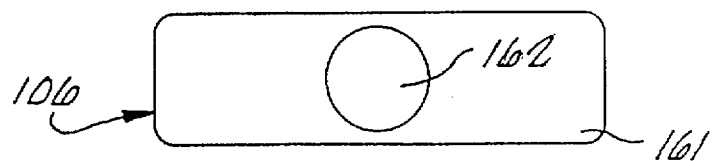
FIG. 48.
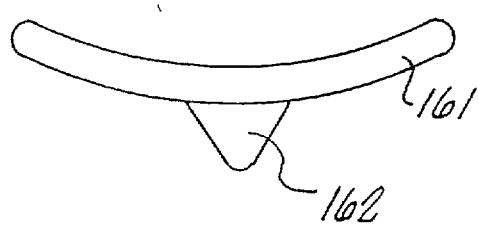
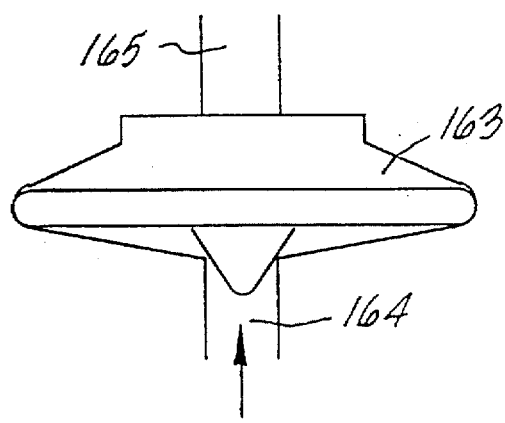
FIG. 49.
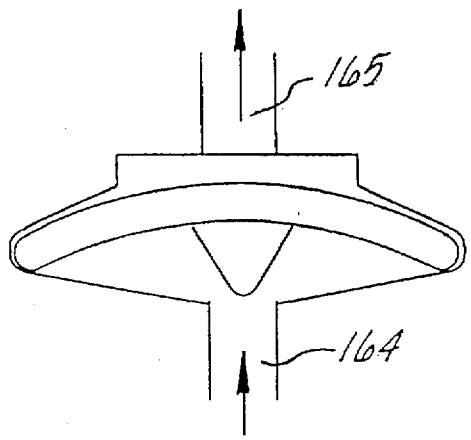
FIG. 50.

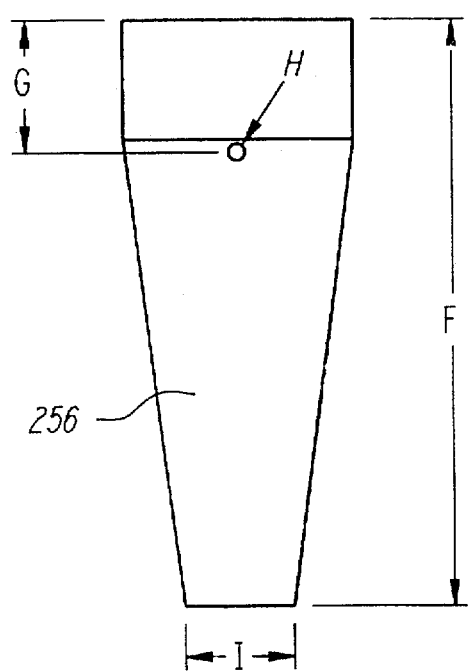
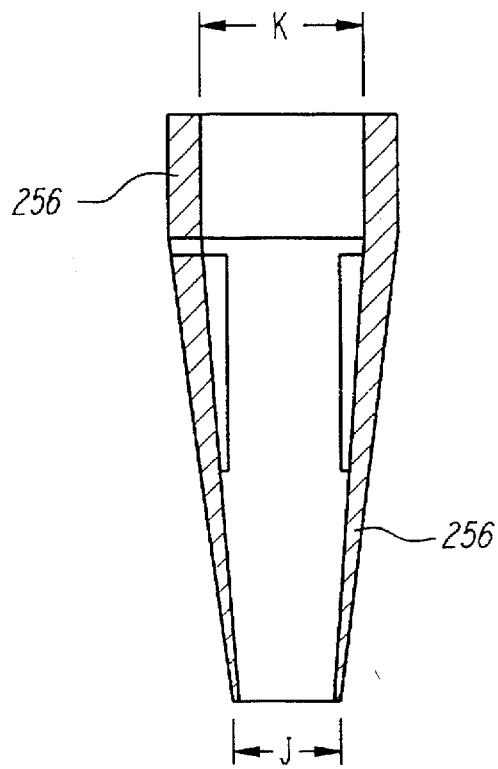
FIG. 70  FIG. 73
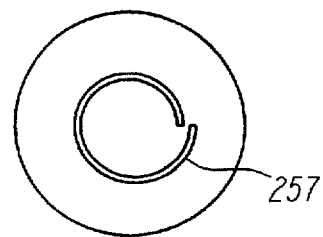
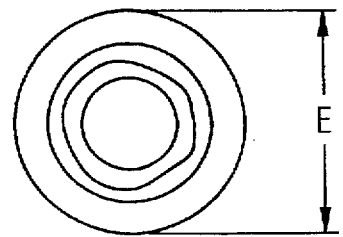
FIG. 71  FIG. 72

MIST GENERATOR

This application is a continuation-in-part of Ser. No. 07/974,801, filed Nov. 12, 1992 now U.S. Pat. No. 5,346,132.

BACKGROUND OF THE INVENTION

The field of the present invention is devices for creating and applying mists, vapors, or sprays from a liquid, in medical, industrial, and household applications.

The eye is perhaps the most sensitive organ of the body. By contrast to other organs, the slightest touch of the cornea may be irritating and painful. Similarly, the membrane which covers the remainder of the eye, the conjunctiva, is so thin and delicate that it is normally invisible unless it becomes irritated. Both the cornea and conjunctiva are normally kept moist by the constant washing action of tears and blinking.

Because of its sensitivity, many common conditions may irritate the eye. Dry or polluted air, wind, bright light, swimming, dust or chemical fumes all produce eye irritation. Similarly, contact lenses are frequently irritating, especially if worn continuously throughout the day.

Surprisingly, few easy to use and effective methods to relax and comfort irritated eyes have been developed. To rid the eye of foreign objects, for example, a saline-filled "eye cup" or eye wash bottle is used. Since both are messy and inconvenient, it is not practical to use either for routine eye comfort. Another method of relieving seriously dry eyes caused by certain eye diseases employs a small specifically formulated prescription rod-shaped solid strip (Lacrisert™) which is inserted under the lower eyelid. Over several hours, the strip dissolves into the tears and produces a soothing liquid film. Since this product is available only by prescription, it is used only in limited and serious eye conditions.

For the vast majority of people, the only method of applying liquid to the eye is perhaps the first method ever invented—the eye drop. Many if not most substances intended for application to the eye, both over the counter (OTC) and prescription, are packaged in a container which has a built in "eye dropper". Unfortunately, dropping drops into the eye is awkward, inconvenient, uncomfortable and potentially dangerous. For any parent who has tried to apply drops of liquid into the eye of a small child, the prospect of repeating this frequently traumatic action is not appealing. Similarly, applying drops into one's own eye, especially if one's manual dexterity is not optimum, can be difficult and unpleasant and potentially dangerous to the eye. For many older people who need to frequently apply eye moistening liquids or eye medications because of chronic eye disease, eye drops can be very difficult to manage because of arthritis, injury or poor hand-eye coordination.

In order to effectively administer a drop to any eye using an eye dropper, the user must position the pointed dropper tip close to the delicate and sensitive cornea. A slightly unsteady hand or sudden movement may cause the tip to hit the eye and cause pain, damage and potentially vision-threatening damage. The awareness of this possibility may be keenly appreciated by observing an average user attempt to self-administer eye drops. For this reason, it is dangerous to use eye drops when the user is in motion or may be bumped in a crowded area. The use of a dropper bottle on an airplane, for example, may subject the user to significant risk given the possibility of an unexpected jolt from air turbulence or a bump from a fellow passenger.

In ocular drug therapy, it is important that the patient deliver the correct amount of drug to the eye. Because of the difficulty of using and properly aiming eye drops, however, some medication usually drips down the face, thus missing its intended therapeutic target. In case of vision-saving anti-glaucoma drugs or antibiotics, under or over-administration of the drug may have serious repercussions.

Due to the potentially vision-threatening nature of many ocular conditions which require prescription medications, strict patient compliance with the physician's recommended dosing schedule is very important. Unfortunately, ocular drugs administered by eye drops are unpleasant and difficult to use for many people which results in relatively poor compliance with the physician's instructions and potentially serious consequences.

For many eye conditions and diseases, incidence increases with advancing age. As age increases, however, the manual dexterity and eye-hand coordination required for self-administration of eye drops may be greatly reduced. It is difficult enough for a young, healthy person to tilt the head back, hold an eye lid open with one hand while trying to aim and drop liquid into the eye with the other hand. For many older people, it is essentially impossible. The fact that many ocular drugs must be administered as often as four times per day further compounds the potential problem. This unfortunate set of common circumstances sets into motion potentially vicious cycle which frequently leads to inadequate use of vision-saving eye medications with potentially catastrophic results. Accordingly, an improved way of delivering eye medication would be of great benefit.

The eye is also very susceptible to accidental injury. The inadvertent introduction of chemicals or foreign bodies into the eye constitutes a potential medical emergency. Rapid intervention by flushing the eye with an inert liquid can potentially prevent irreversible loss of vision. Unfortunately, access to eye wash bottles or fountains in schools, laboratories, industrial settings, at home or during recreational activities is sometimes limited. A portable and easy to use eye wash device would be very useful to help reduce eye injury from foreign chemicals or objects.

Accordingly, there remains a need for a device for safely, accurately and conveniently administering drugs or other substances to the eye.

Consumers are increasingly recognizing that cosmetics and personal skin care products have the ability to provide more than just a superficial change in skin appearance. Cosmetics may also provide protection against the potentially damaging ultraviolet rays of the sun and can protect against the irritating and potentially skin-threatening environmental conditions which lead to irritation and premature signs of aging. For this reason, consumers recognize that to obtain optimum benefit, skin-protective cosmetics must be applied more often then only during the morning and evening rituals common to many customers.

It is, however, awkward and inconvenient for many people to carry multiple jars and bottles during the day and equally troublesome to open containers which may spill and apply cosmetics or fragrances in many social or business environments.

Many women and men would like to use skin care products throughout the day but do not because of the inconvenience of conventional application methods. Most skin care products require the customer to use their fingers or hands to apply and evenly spread the product on the skin. Touching the skin with the fingers, especially for acne-prone people, increases the chances of skin irritation and blemishes. Rubbing products into the skin can also leave greasy or oil residues which may remain on the hands and can be transferred to papers, equipment or other people and forces customers to go to the restroom to wash their hands. This inconvenience results in many people limiting their use of skin care products to the home.

Similarly, the approximately one in ten Americans who wear contact lenses are acutely aware of chemical residues on their hands which may contaminate the lenses when they are removed and cleaned during the day. This concern is especially applicable to skin "treatment" products in general and sun screen products in particular since many adhere to the skin for extended periods of time even after exposure to water. For this reason, many contact lens wearers do not use sun screen or skin care products during the day unless they have ready access to soap and water.

Another group of people may find it cumbersome or unwieldy to apply skin care products due to their particular environment. Skiers, for example, frequently need facial moisturizers and sunscreens due to the dry, windy and ultraviolet-rich environment of the mountains, but find it awkward to carry and use multiple bottles or tubes of products. Airline travelers have a similar need for frequent facial moisturization due to the low ambient humidity of airplane cabins, but many find it inconvenient to carry products which may leak or spill in the crowded, depressurized cabin environment.

Many men and women are exposed to low humidity environments which increase transepidermal water loss and produce dry, chapped and irritated skin. Air conditioning, forced air heating, airplane travel, high altitudes, desert climates and many other factors result in the frequent need for facial moisturizers. In many of these environments, however, it is not convenient to carry or use moisturizing products.

During the last several years, consumers have also become acutely aware of the role of ultraviolet radiation in producing sun burn and long-term skin photoaging. Both men and women gravitate towards sun protection products with "light", non-greasy formulations which are invisible during wear.

A shortcoming of known aerosol and pump sprays for delivering skin care, fragrances and cosmetic products is the inability to accurately control the amount of spray or mist produced. In addition, the pattern and shape of the spray can be unpredictable, irregular, and vary with the pressure of the propellant or pumping action. Spray velocity and droplet size can also be inconsistent and difficult to control.

In a conventional pump, the spray can be difficult to aim and the spray pattern is poorly focused. Furthermore, pump sprays deliver only a fixed amount of liquid which may exceed the amount desired by a consumer. This lack of control of pump sprays frequently results in products staining clothes, getting into the hair or being sprayed in the eyes or in areas of skin not desired.

Many "high-end", expensive cosmetic formulations use ingredients which are believed to provide skin-rejuvenating or protection properties. These ingredients include lipids (eg. ceramide derivatives); glycosaminoglycans (mucopolysaccharides, eg. hyaluronic acid); "exotic proteins" (eg. fibronectin, placental proteins); nucleic acids, vitamins (eg. vitamins C and E), among others.

In many instances, these ingredients are formulated in encapsulated, unit dose vials or capsules to protect the products from exposure to air or the environment which may oxidize or otherwise chemically degrade the ingredients. However, these products can be difficult to apply without waste and are relatively expensive.

Many chemicals used in cosmetics can oxidize due to contact with oxygen in the air. Instability of cosmetic ingredients can limit the circumstances in which desired ingredients can be used or may prevent their use entirely. For example, ascorbic acid which has been reported to have beneficial skin-protective effects in humans is unstable when in solution and exposed to air. Many other ingredients derived from "natural" sources such as peptides, vitamins and skin lipids have similar instability when formulated in conventional products. There is accordingly a need for an improved way of applying cosmetics and other skin care products.

Preservatives in cosmetics and skin care products produce skin irritation in many sensitive skin consumers. Nevertheless, conventional application methods, especially those requiring the user to touch the product with the fingers, require the use of preservatives since microbial contamination is difficult to prevent. Accordingly, there is a need for a device which can hold and dispense preservative-free skin care products while keeping products free of microbial contamination.

Lubricants, paints, solvents, etc. are frequently applied to many products found in the home. Frequent sites of lubricant application include: door hinges, door locks, nuts and bolts and screws, fans, motors, drawers, windows and many mechanical devices. A common feature of all of these uses is the small size of the lubricated area and its frequent location adjacent to rugs, curtains, walls or other objects which would be stained or otherwise harmed by the inadvertent contact with lubricants.

Conventional aerosol sprays used to dispense many lubricants are notorious for their tendency to splash, ricochet and drip during application. Moreover, these aerosol sprays can be difficult to aim and control. Some aerosol sprays also use propellants which are damaging to the environment. Thus, there remains a need for a device for spraying lubricants, paints and other liquids which avoids these disadvantages of conventional aerosol sprayers.

SUMMARY OF THE INVENTION

The present invention is directed to a mist generator for creating a spray of mist or vapor from a liquid medium. To this end, a spinning rotor draws a liquid medium into a chamber within the rotor. The liquid medium is centrifugally moved through one or more mist holes through the rotor, forming a spray of fine droplets of liquid medium. Multiple mist holes may be vertically aligned (on the same plane of rotation) on the rotor, or they may be vertically offset. The spray consists of droplets which are large enough to deliver a measurable quantity of liquid within several seconds, to wet e.g., an eye or skin surface. A visible light beam aids in aiming the spray. The liquid medium is contained within a modular sealed package and may be pumped to the rotor. Preferably the rotor chamber tapers conically outwardly from the bottom to the top.

Accordingly, it is an object of the invention to provide a mist generator for medical, skin care, household and industrial uses.

BRIEF DESCRIPTION OF THE DRAWINGS

Other objects and features of the present invention will become apparent from the following detailed description taken in connection with the accompanying drawings. It is to be understood, however, that the drawings are designed for the purpose of illustration only, and they are not intended as a definition of the limits of the invention.

In the drawings, wherein similar reference characters denotes similar elements throughout the several views:

FIG. 5 is a right side elevational view thereof;

FIG. 6 is a front elevation thereof;

FIG. 18A is an exploded side elevation view of non composite pump and cartridge modules;

FIG. 18B is a side elevation view of a nebulizing module for use with the non composite cartridge and pump modules of FIG. 18A;

FIG. 18C is a side section view of the retainer clip which holds the cartridge module of FIG. 18A to the nebulizing module of FIG. 18B;

FIG. 19A is an exploded rear side elevation view in part section of the non composite pump and cartridge modules of FIG. 18A;

FIG. 19B is a rear elevation view of the nebulizing module of FIG. 18B;

FIG. 19C is a rear elevation view of the retainer clip of FIG. 18C;

FIG. 32 is an exploded fragment view in part section of the motor, rotor, seal and optical spacer block shown in FIG. 30;

FIG. 33 is an enlarged perspective view fragment of the rotor of FIG. 30;

FIGS. 47–50 are schematic views of the present check valves;

FIG. 70 is a front view of an alternative preferred mist rotor;

FIG. 71 is a bottom view thereof;

FIG. 72 is a top view thereof; and

FIG. 73 is section view thereof.

DETAILED DESCRIPTION OF THE PREFERRED EMBODIMENTS

Figure 1:
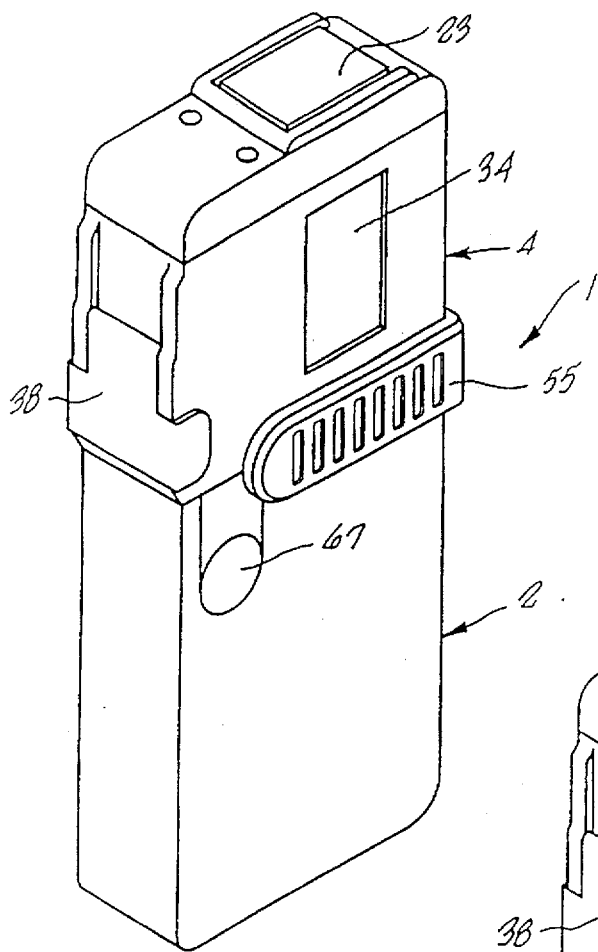
FIG. 1 is a perspective view of the present mist generator.
Figure 3:
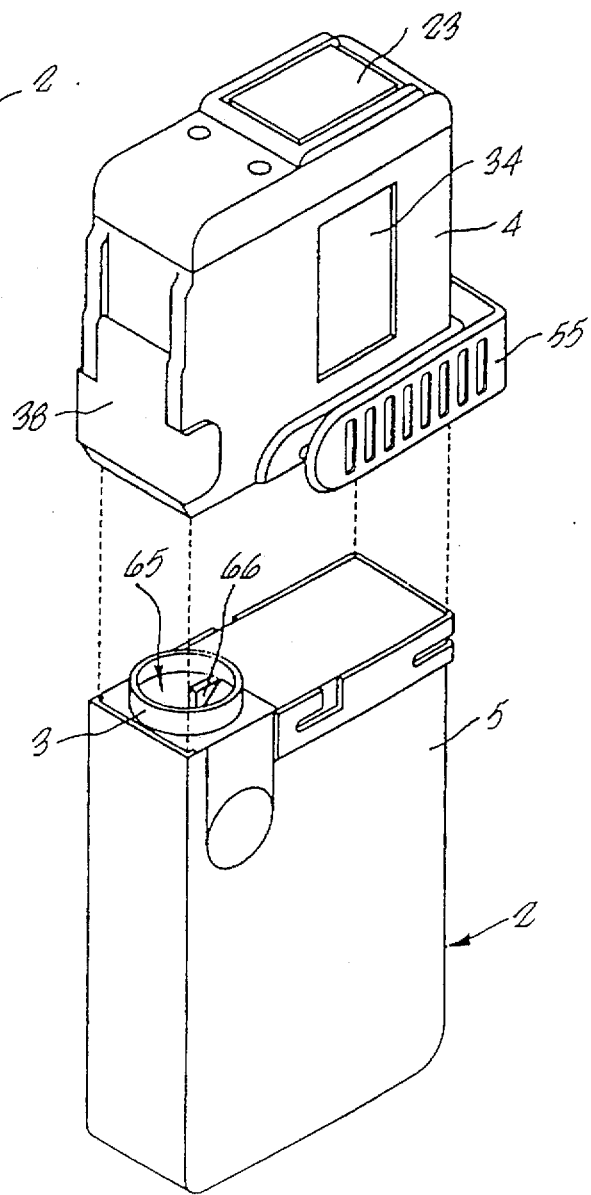
FIG. 3 is a partially exploded perspective view of the mist generator of FIG. 1.
Figure 2:
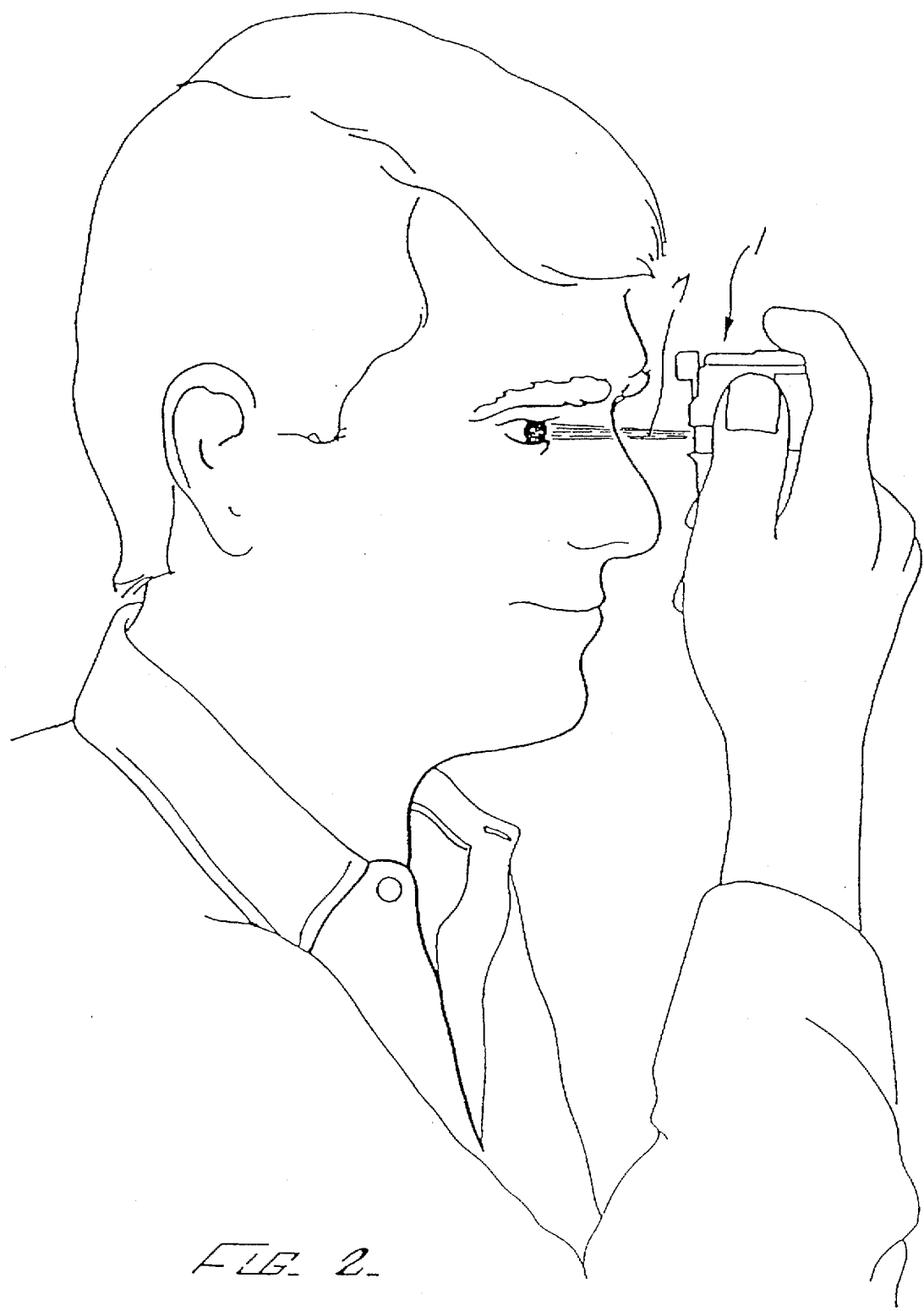
FIG. 2 is a perspective view showing use of the present mist generator.
Figure 4:
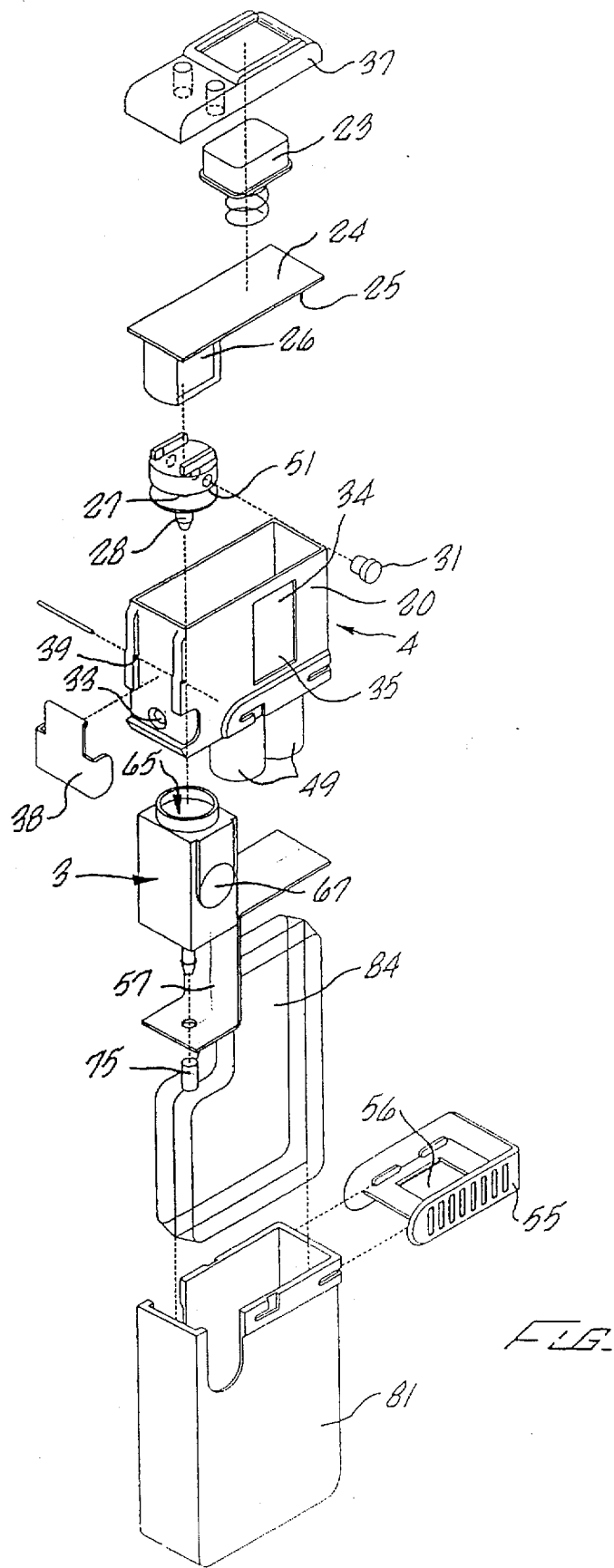
FIG. 4 is a fully exploded perspective view thereof.

Turning now to the appended drawings, as shown in FIGS. 1–3, the present mist generator 1 is a portable self-contained and compact device for generating a beam or spray of mist. As shown in FIG. 2, the mist generator 1 may be used to apply a spray 7 of liquid to the user's eye. Referring to FIGS. 3 and 4, the present mist generator 1 preferably is of modular construction and includes a nebulizing module 4 attachable to a cartridge module 2. The cartridge module contains a pump module 3 which may be permanently attached to and disposable with the cartridge module. Alternatively, the pump module may be separable from the cartridge module 2 and reusable. When the cartridge module is permanently attached to the pump module, the resulting combination is termed a "composite" module (eg. composite cartridge/pump module 5.)

Figure 16:
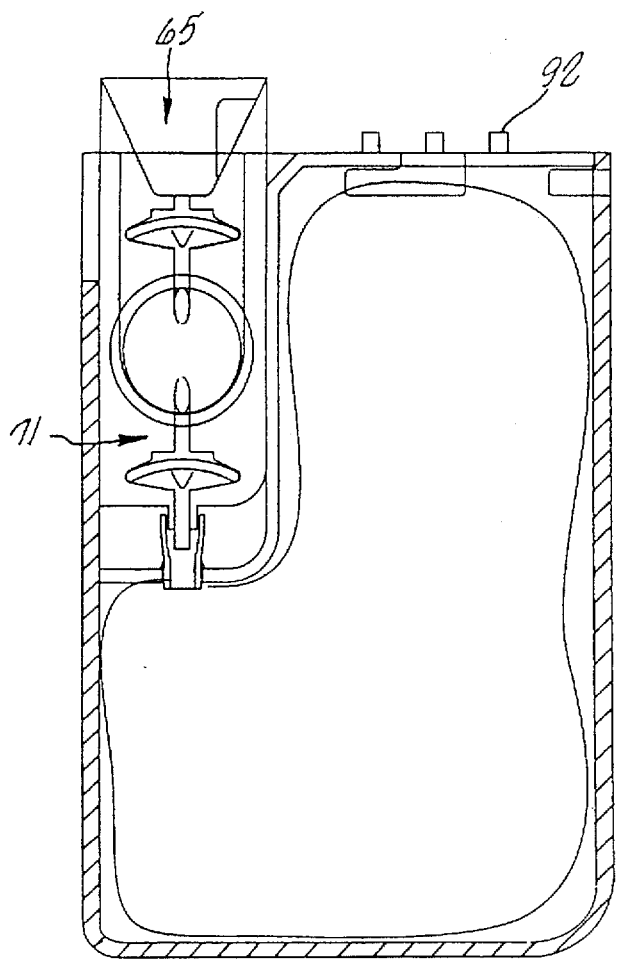
FIG. 16 is a right side elevation view in part section of a composite pump and cartridge module.
Figure 17:
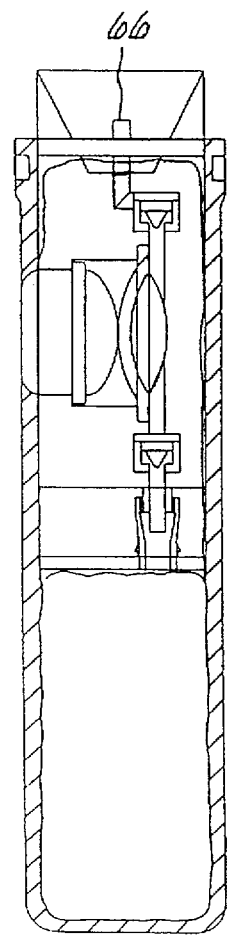
FIG. 17 is a rear view thereof in part section.

The modular design provides a high degree of flexibility and potential cost savings. In situations where the mist generator device is used repetitively with a single product (e.g., a fragrance or a sunscreen), only the cartridge module 2 as shown in FIGS. 18 and 19, needs to be replaced when it is empty while the pump module 3 can be reused. Similarly, for many skin care products, a single pump module 3 may be used in conjunction with multiple cartridge modules 2 over many months. By contrast, for over the counter or prescription drug dispensation where the ultimate in cleanliness is important, the single disposable composite pump and cartridge module 5, having the pump module 3 permanently attached to the cartridge module 2, as shown in FIGS. 3, 16 and 17 is used.

Referring to FIGS. 4, 7, 9 and 30, the nebulizing module 4 includes a mist rotor 28 attached to the shaft 27 of a high speed miniature electric motor 26. The motor 26 is contained within a motor chamber 41 formed within a nebulizing module housing 20. A dual-contact momentary rocker off-on switch 23 is positioned on top of the separate housing 37 which, in turn, is on top of the nebulizing module housing 20. A control and communication circuit 25 is supported within the nebulizing module housing 20 over the motor 26 and below the switch 23. Switch contacts 24 link the switch 23 to the control and communication circuit 25.

Figure 9:
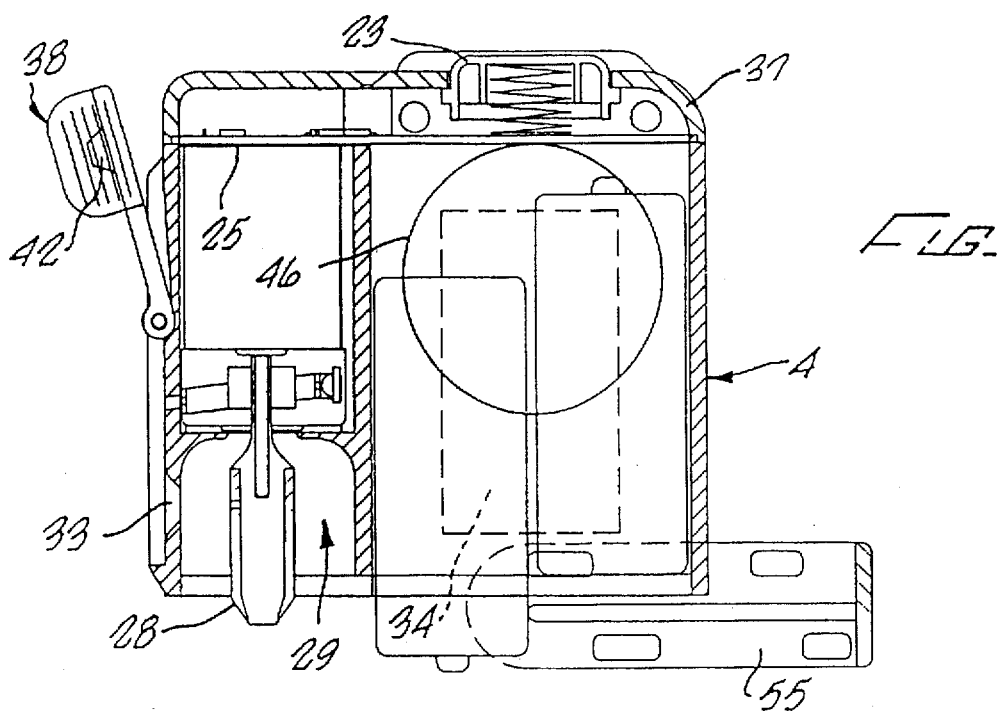
FIG. 9 is a right side section view of a nebulizing module.
Figure 10:
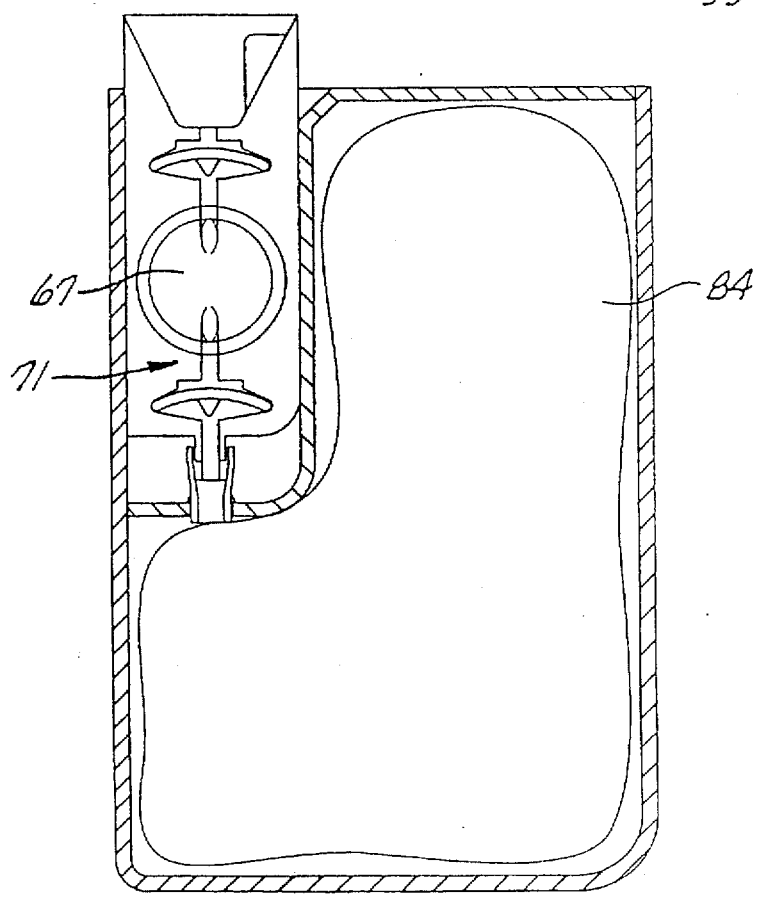
FIG. 10 is a right side section view of a composite cartridge and pump model.
Figure 11:
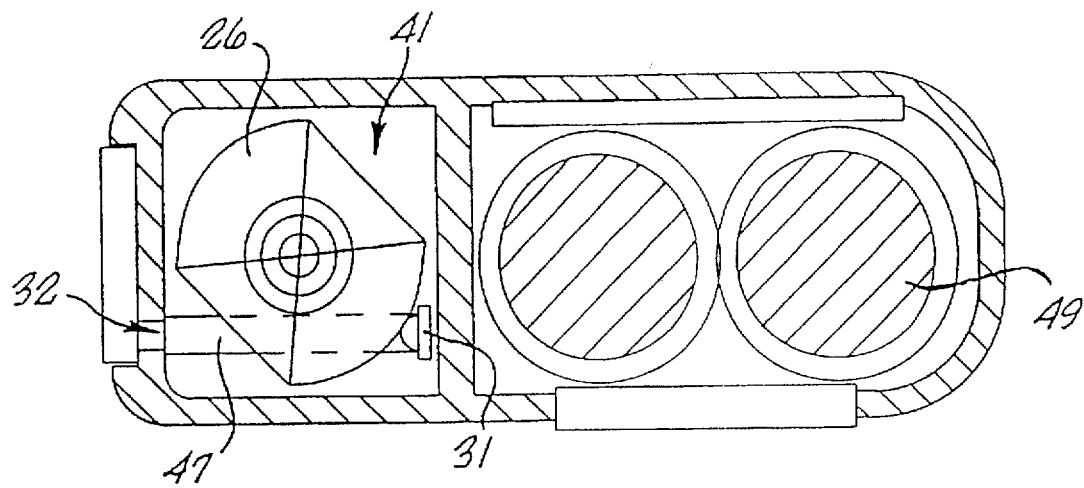
FIG. 11 is a section view taken along line 12—12 of FIG. 7 depicting an embodiment having a light pipe and an LED arrangement.

N-size alkaline batteries 49 are contained within a battery compartment 21. A retainer clip 55, as shown in FIGS. 3, 5 and 9, connects the nebulizing module with the pump/cartridge module 5. To replace the pump/cartridge module, the user grasps the ribbed slide on both sides of the device and pulls back until a detent is reached. At this position, the two modules can be pulled apart. To access the battery compartment, the user must push up slightly on the slide to overcome the battery spring contacts in order to release the detent and then must further slide the retainer outwards to expose the batteries. The retainer therefore acts as a battery access door. The slide mechanism also contains a conducting battery jumper plate 56 which electrically connects the two batteries together. A speaker or sound transducer 46 is supported within the battery compartment and connected to the control and communication circuit 25. Openings may be provided in the nebulizing module housing 20 overlying the sound transducer 46. An alpha numeric display 34, preferably a liquid crystal or LED display, is positioned within the battery compartment and the nebulizing module housing 20. A display window 35 within the nebulizing module housing 20 facilitates viewing the display 34.

Figures 7, 8:
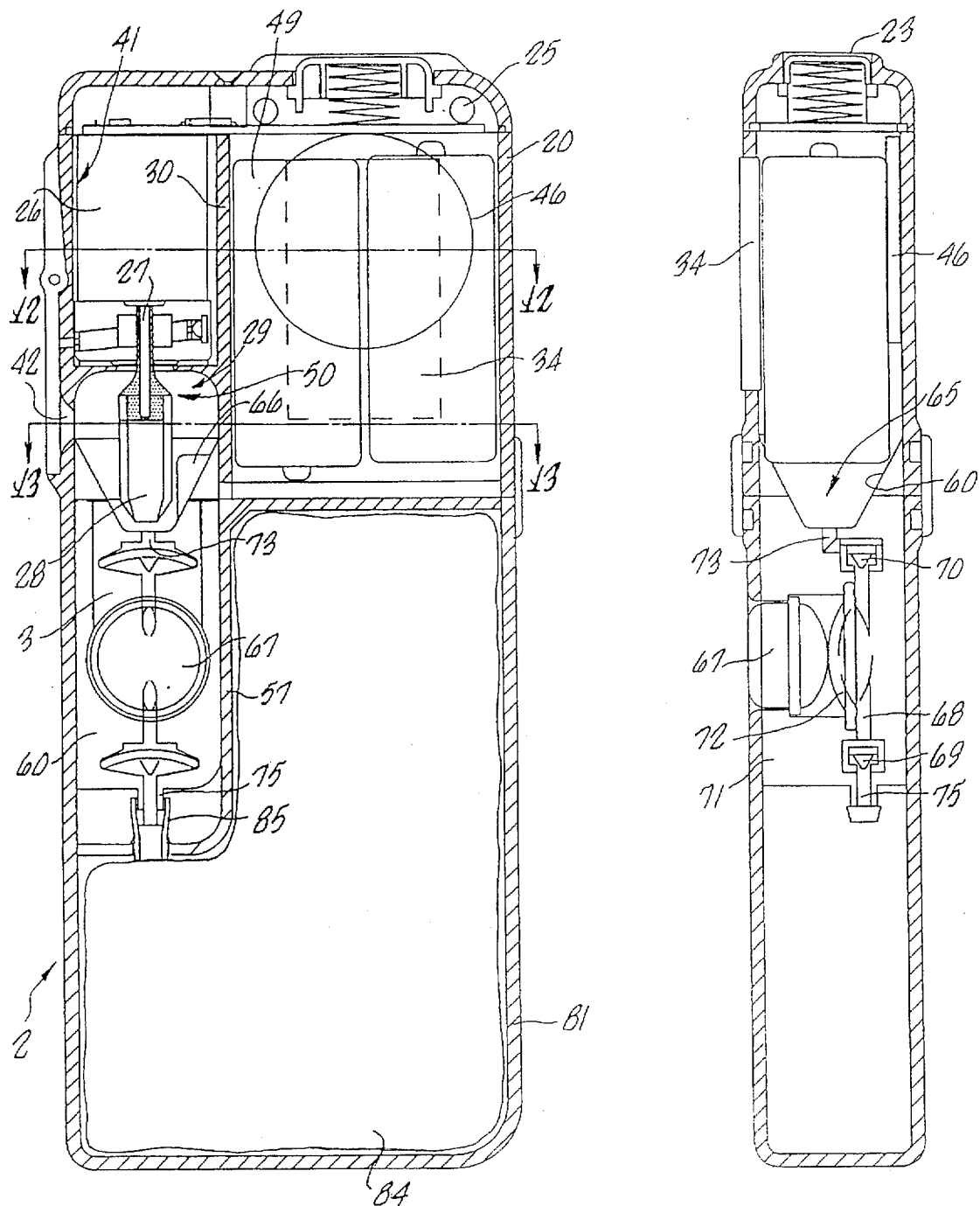
FIG. 7 is a partial right side section view of the mist generator of FIG. 1.
FIG. 8 is a partial rear section view thereof.
Figure 28:
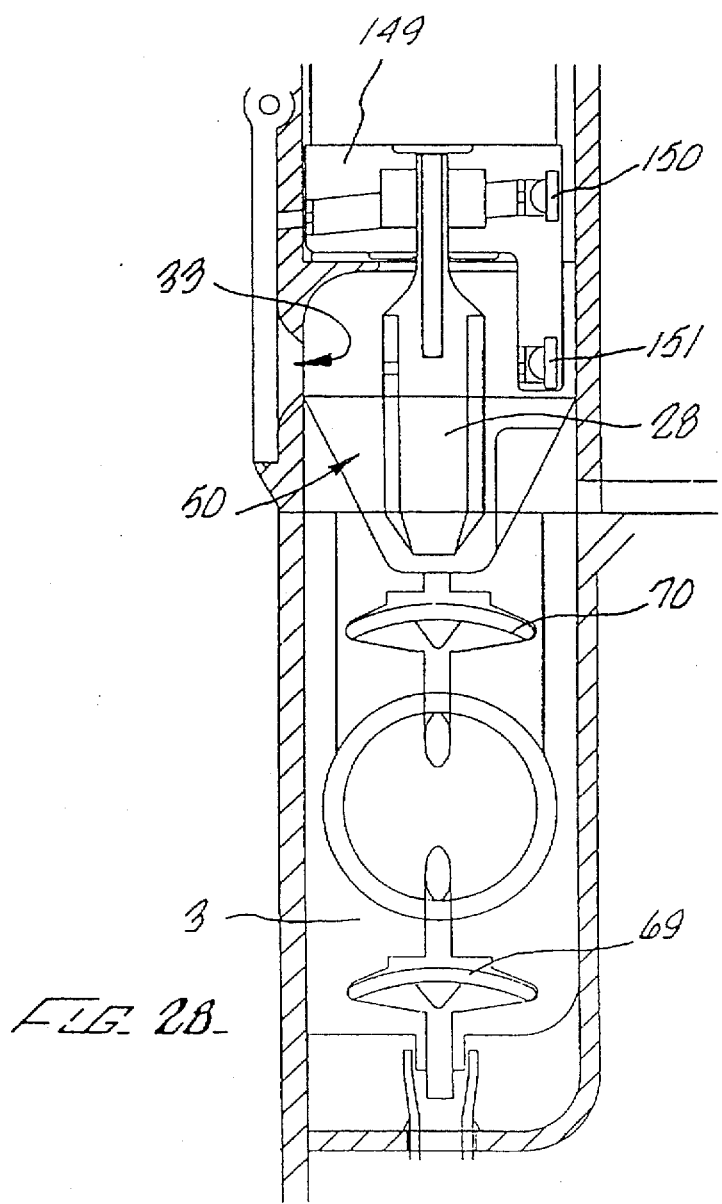
FIG. 28 is an enlarged section view fragment of an alternative mist spray aiming system.
Figure 30:
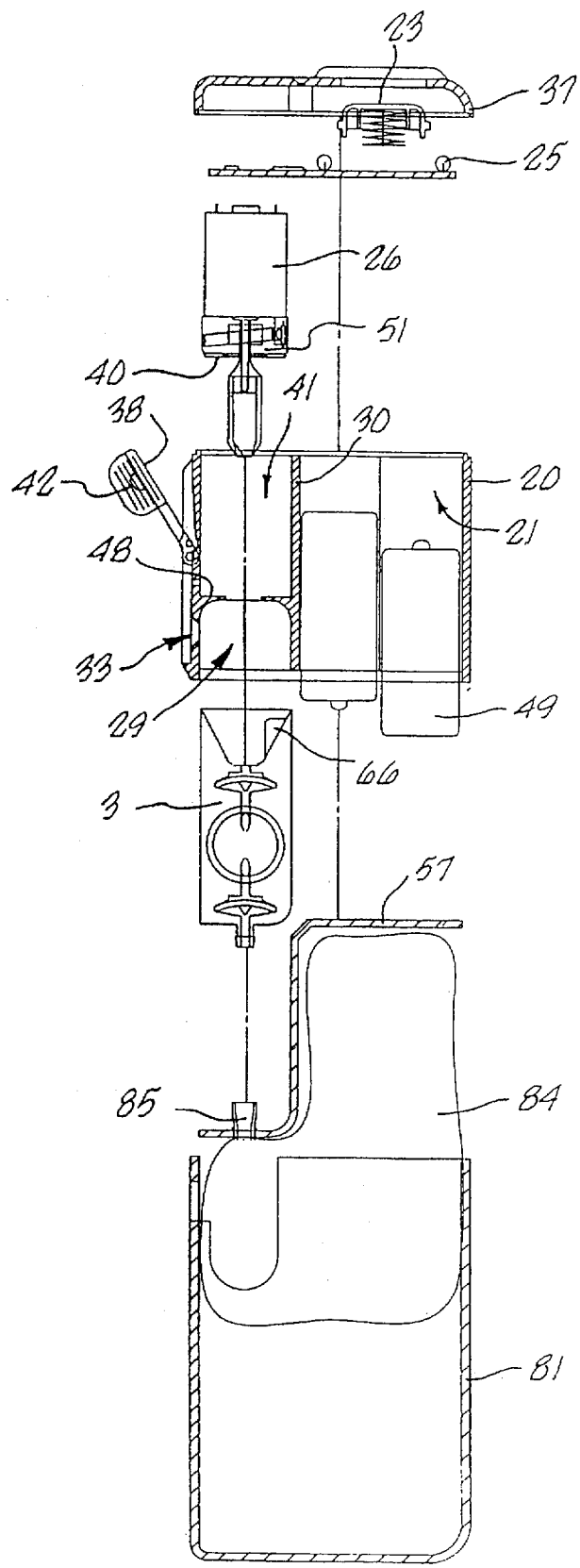
FIG. 30 is an exploded view in part section illustrating assembly of the nebulizing, pump and cartridge modules.
Figure 31:
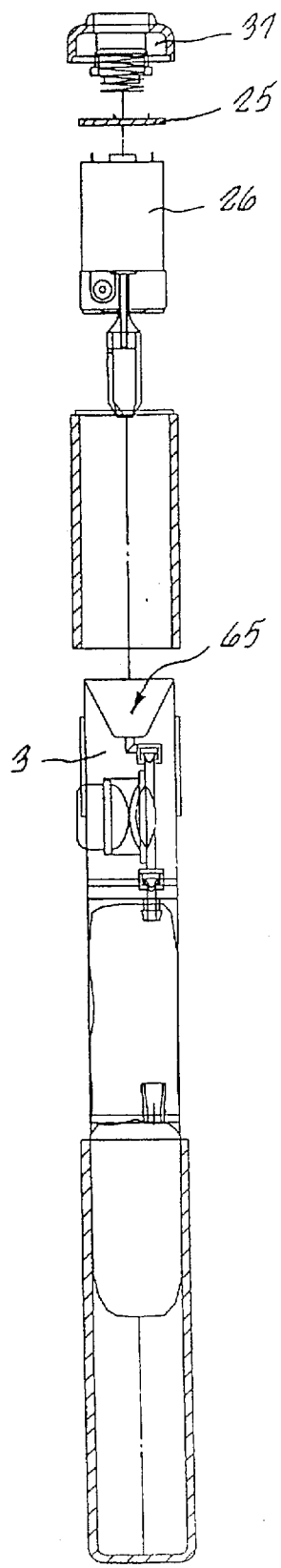
FIG. 31 is a rear side view thereof.
Figure 34:
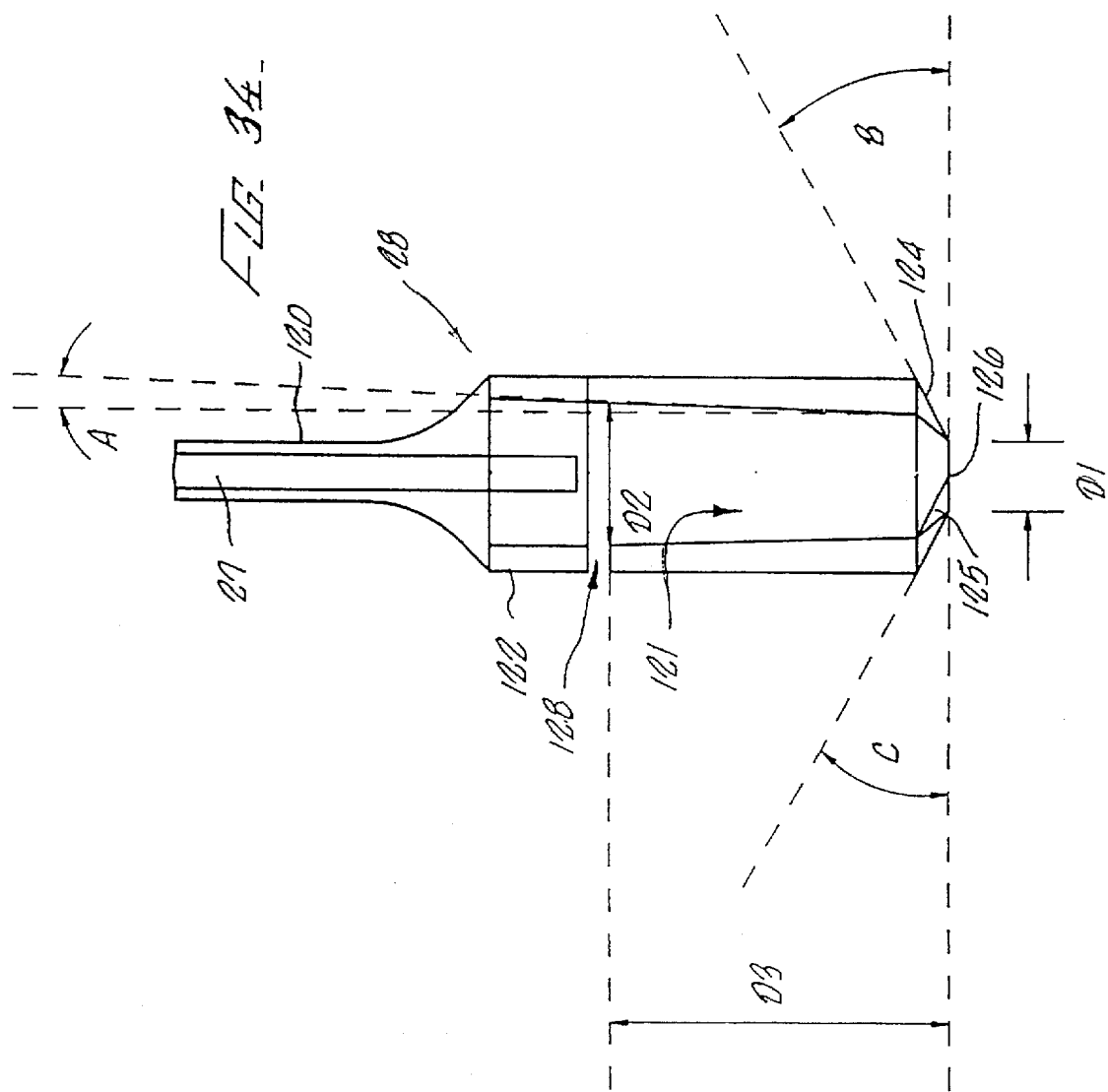
FIG. 34 is an enlarged schematic view of mist rotor showing preferred geometries.
Figure 35:
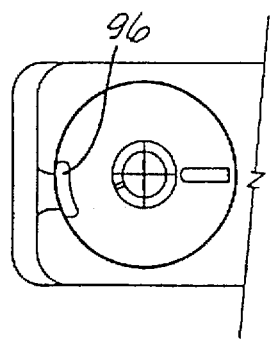
FIG. 35 is a plan view fragment of a mist chamber closed off by a safety shield.
Figure 36:
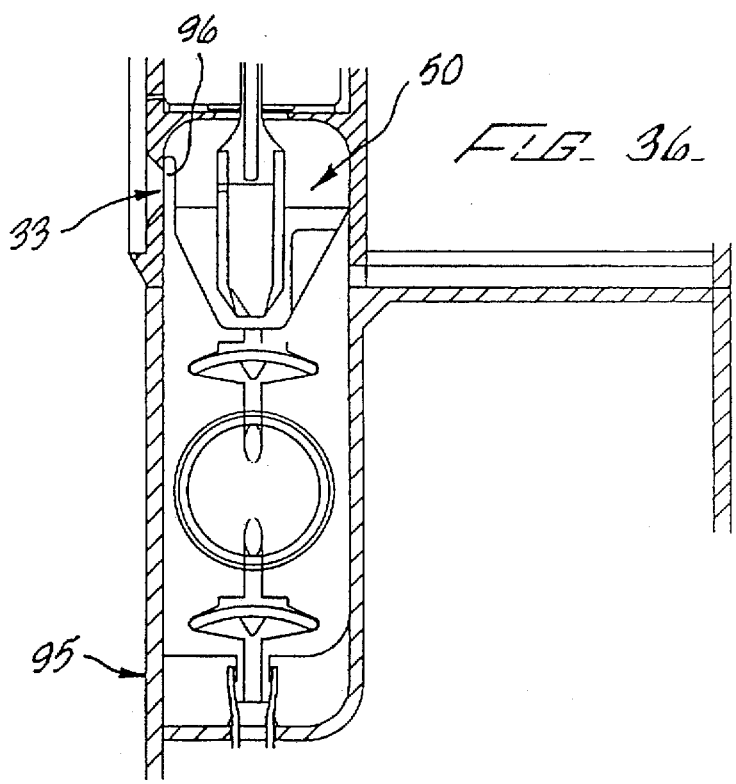
FIG. 36 is a section view thereof.
Figure 37:
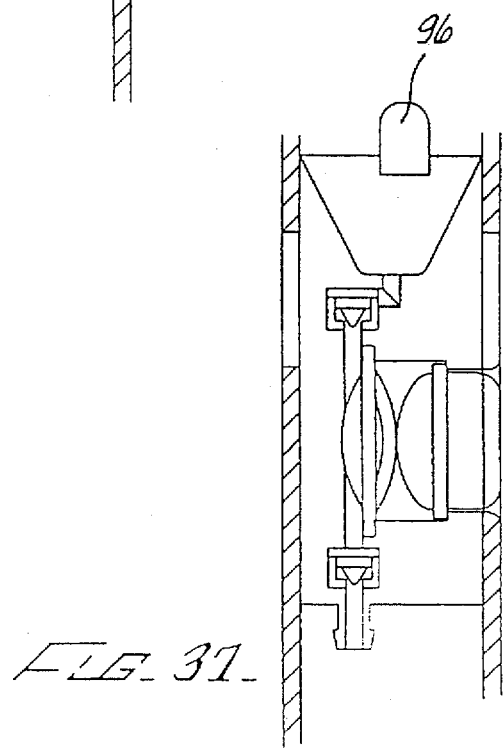
FIG. 37 is a front elevation view fragment of an installed cleaning and disinfection module.
Figure 39:
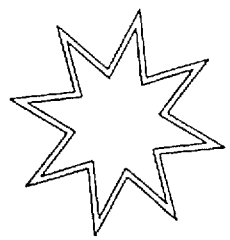
FIG. 39 is a fragment plan view of the enzymatic insert.
Figure 40:
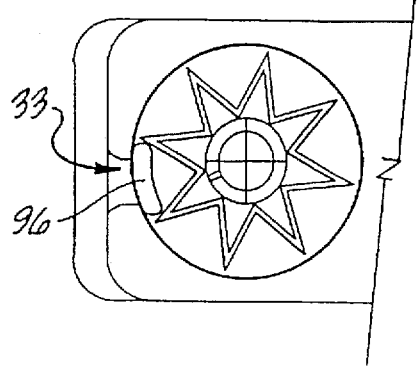
FIG. 40 is a plan view of the enzymatic insert installed in the module of FIG. 38.
Figure 41:
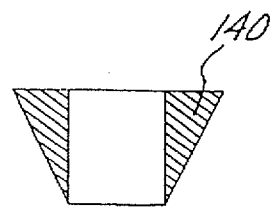
FIG. 41 is a section view of the enzymatic insert.
Figure 38:
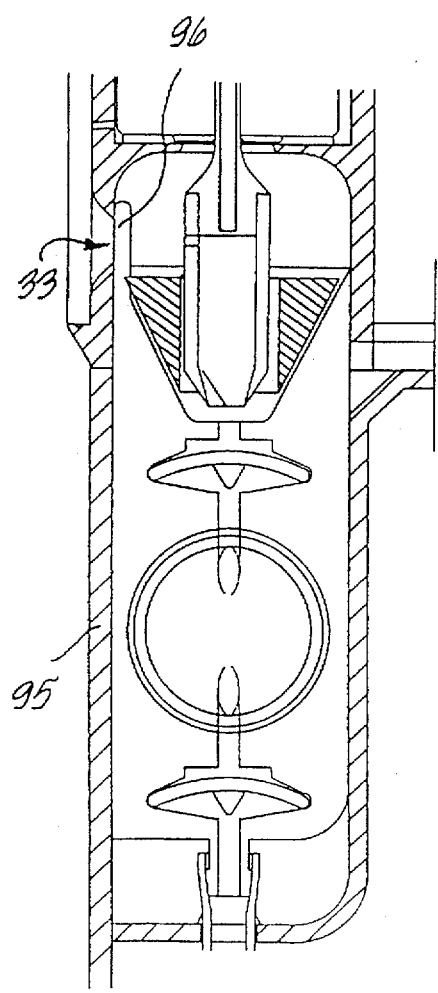
FIG. 38 is a section view fragment of an installed cleaning and disinfection module including an enzymatic insert.
Figure 42:
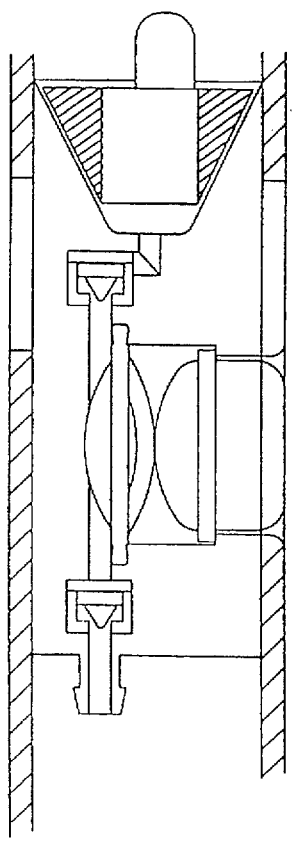
FIG. 42 is a front elevation view in part section of the enzymatic insert installed within a cleaning and disinfection module.
Figure 43:
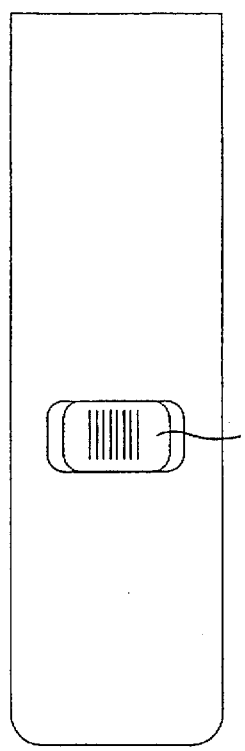
FIG. 43 is a rear elevation view of an alternative embodiment for dispensing two separate liquid mediums separately or mixed together.
Figure 44:
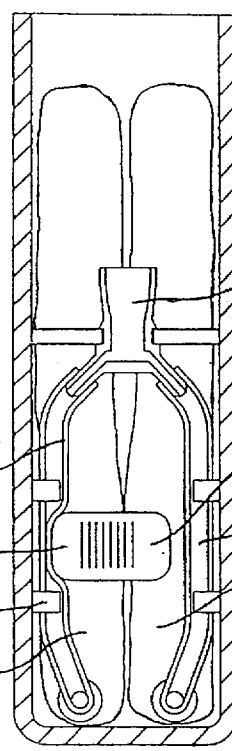
FIGS. 44, 45 and 46 are partial section view fragments showing the operation of the embodiment of FIG. 43.
Figure 45:
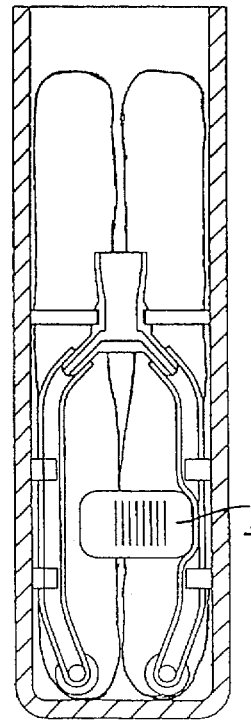
Figure 46:
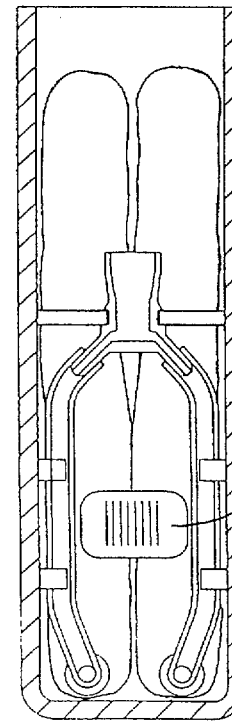
Figure 51:
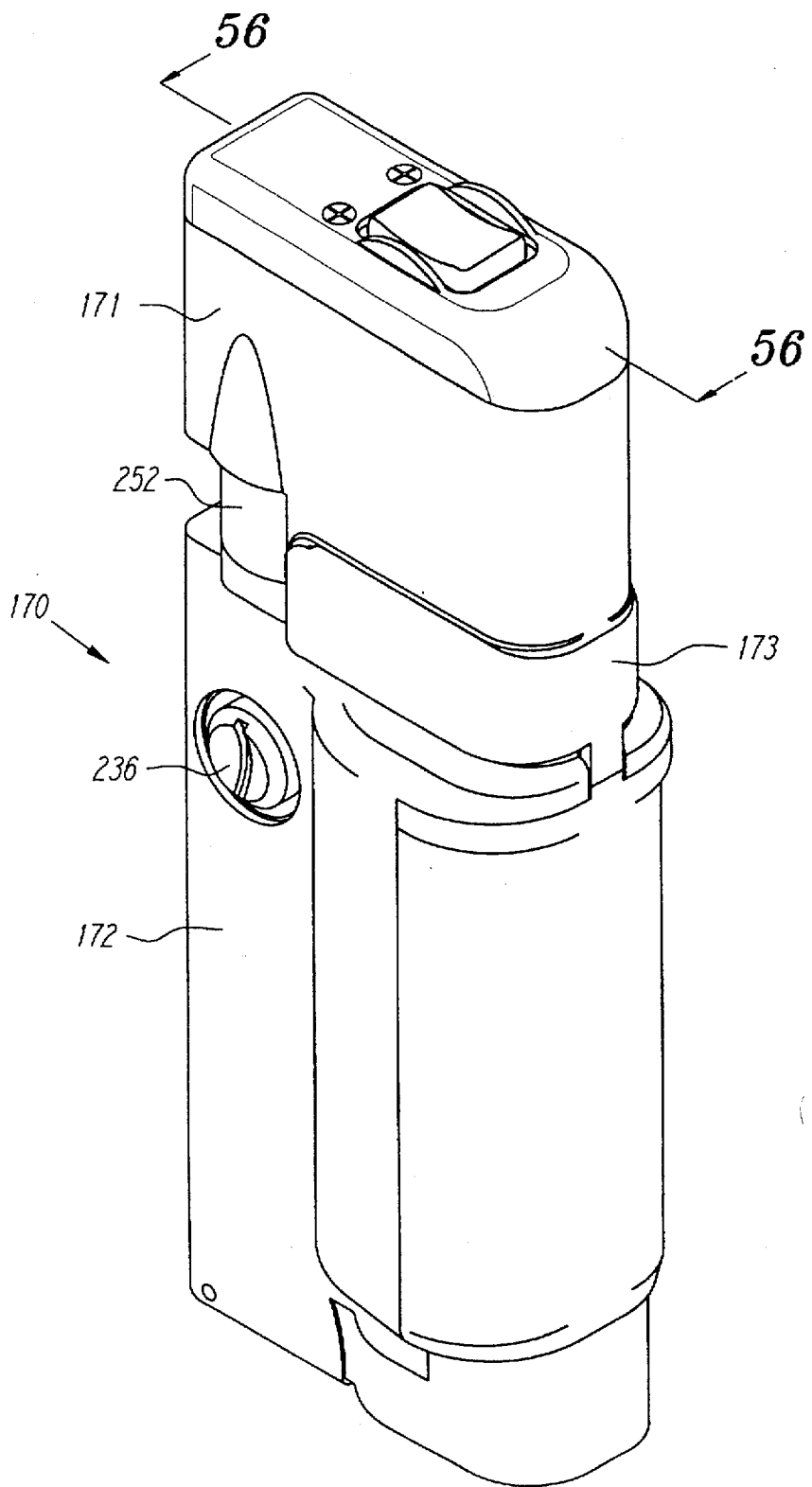
FIG. 51 is a perspective view of an alternative embodiment having a reservoir module which accepts standard medication bottles.
Figure 52:
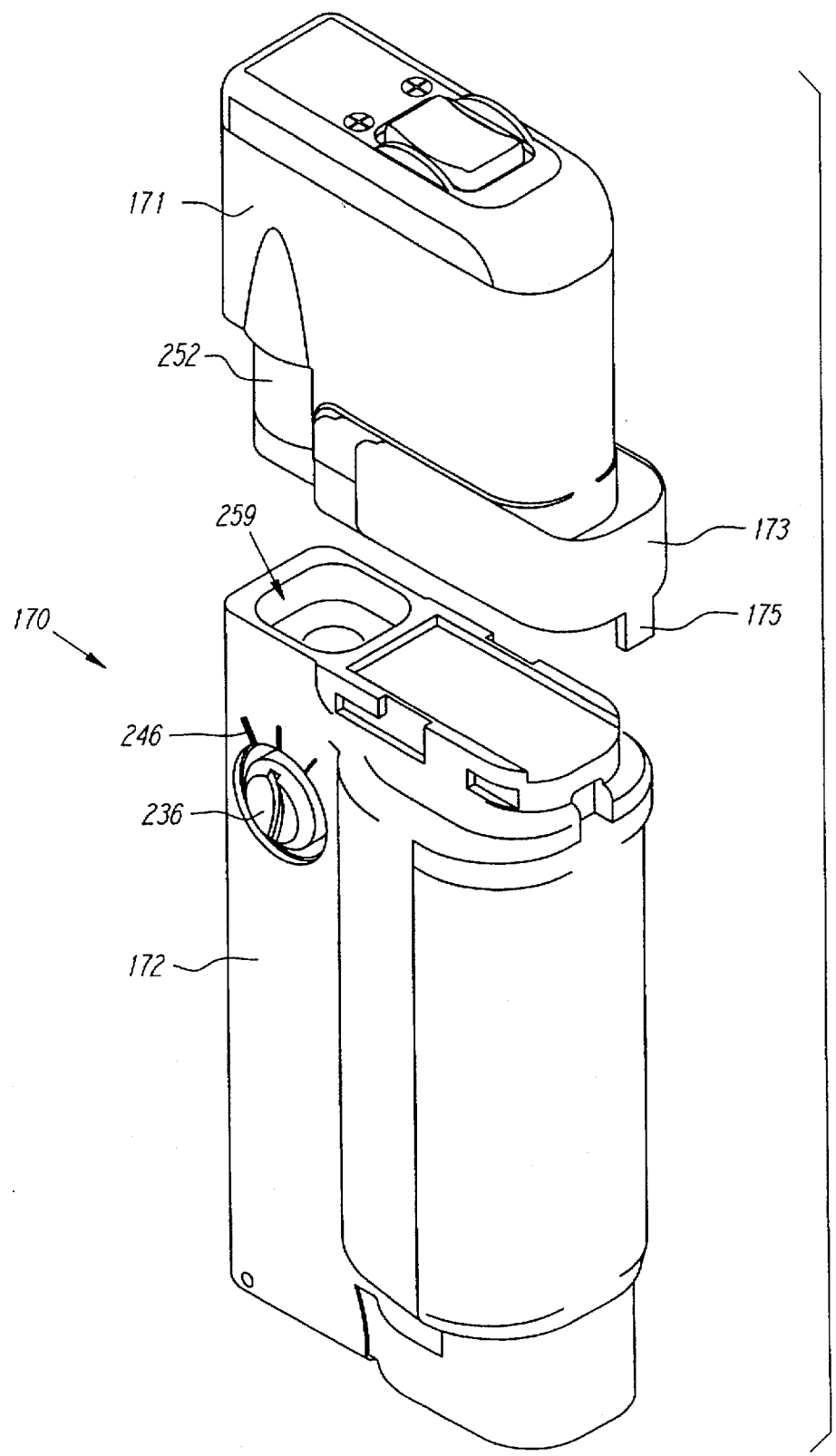
FIG. 52 is an exploded perspective view of the embodiment of FIG. 51, showing the nebulizing module separated from the reservoir module.
Figure 53:
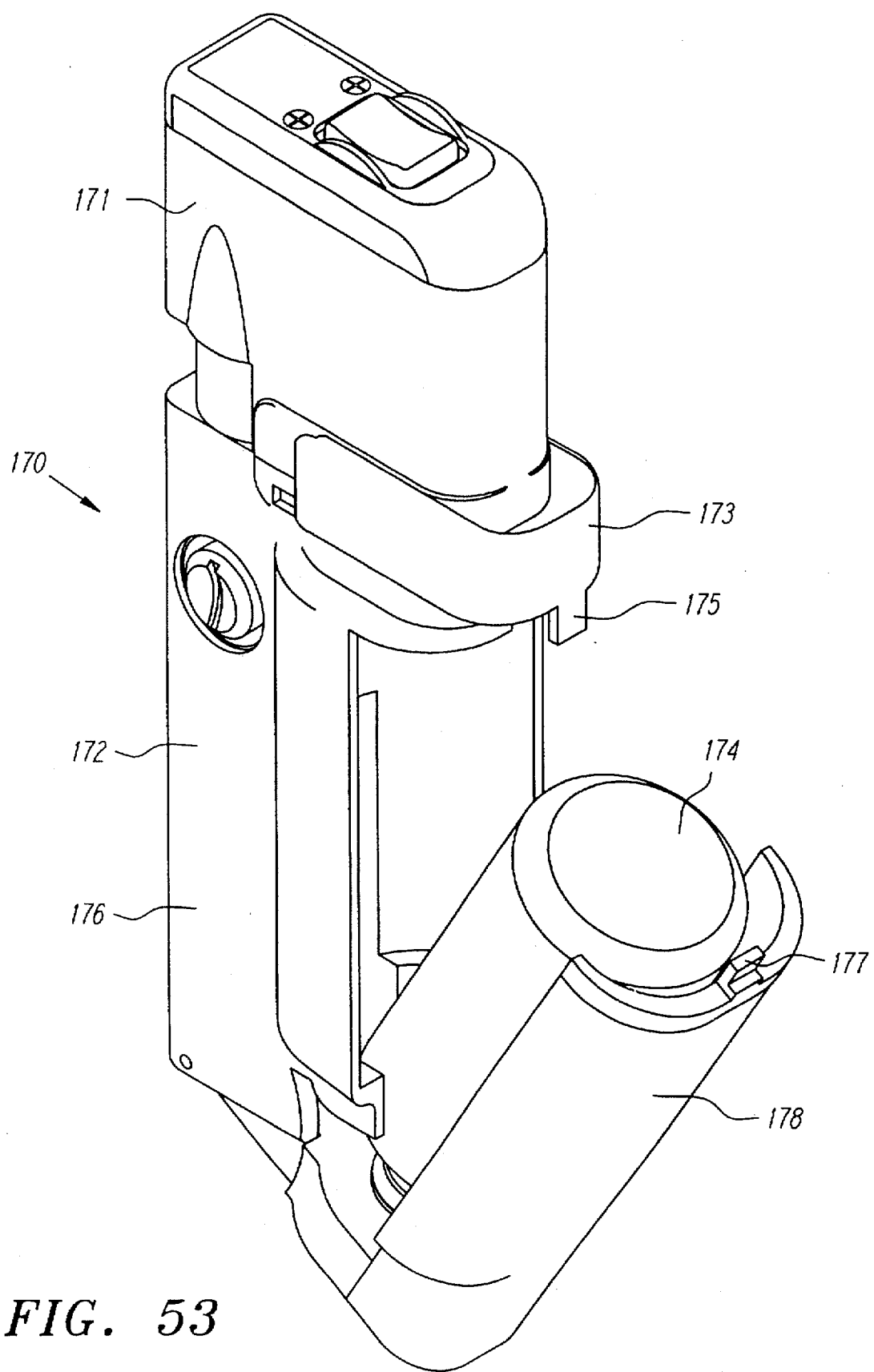
FIG. 53 is a perspective view thereof showing the reservoir module in the open position.

Referring to FIGS. 9 and 30, the top of the nebulizing module housing 20 is preferably provided as a separate housing cover 37. The nebulizing module housing 20 has an interior wall 30 separating the motor chamber 41 from the battery compartment 21. Horizontal walls 48 separate the motor chamber 41 from an upper mist chamber 29, and form a support surface for the optical spacer block which, in turn, supports the motor 26. A mist port 33 extends through the nebulizing module housing into the upper mist chamber 29. A mist port cover 38 is attached to the nebulizing module housing 20 at a hinge joint 39, and is pivotable from a closed position, as shown in FIGS. 4, 7 and 30, wherein the mist port cover 38 has a rubber surface which engages and seals the mist port 33 (as shown in FIGS. 4, 7, and 28) to an open position, as shown in FIG. 9. A conically tapering plug 42 on the mist port cover 38 engages and seals against the mist port 33 when the cover 38 is closed, to prevent any leaking, regardless of orientation, as shown in FIGS. 7 and 30.

Figure 24:
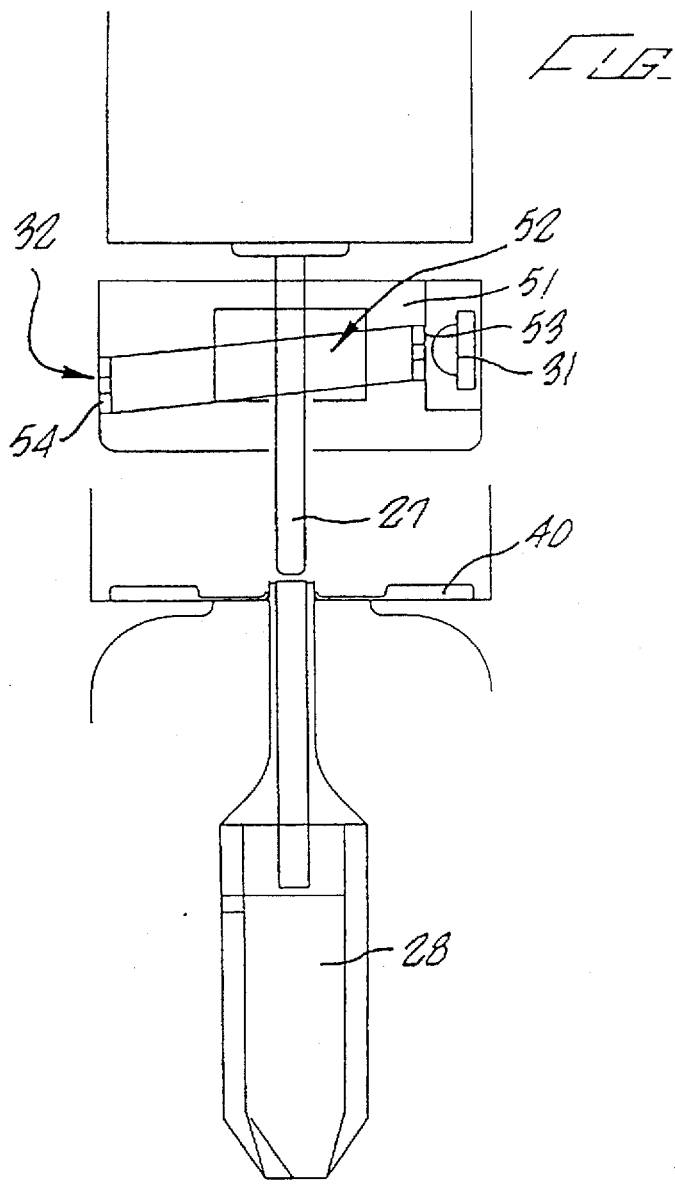
FIG. 24 is an enlarged side elevation view fragment of a mist rotor and seal.

The motor shaft 27 is inserted into one end of the mist rotor which extends through an elastomeric type seal 40 which separates the motor chamber from the mist chamber 50, as shown in FIGS. 7 and 24. The seal 40 has thin knife edges which contact the rotating sleeve and provide a seal between the two chambers without producing appreciable frictional drag.

Referring to FIGS. 9, 11, 12 and 24, an LED 31 is electrically connected to the control and communication circuit and is contained within an optical spacer block 51 upon which rests the motor 26 in the motor chamber 41. The optical spacer block contains an LED port 32 and serves to orient the LED so that its illumination is properly directed to aid in aiming the mist beam.

An LED chamber or tunnel 52 is angled slightly downward from the horizontal and extends through the optical spacer block 51 and holds the LED and precisely aims it toward the mist-impacting point. Depending on the use (e.g., ocular or skin/lubricant), the LED may be positioned at different positions with the LED tunnel. For example, for skin/lubricant designs, the LED will have a rather broad dispersal pattern to match the mist shape. In this instance, the LED would be positioned near the left side of the tunnel closest to the LED port.

By contrast, for ocular uses, the LED and mist beams are very narrow and the LED beam must be collimated and aimed by the mist port aperture and/or internal light apertures which allow the light beam to be visible from only limited angles. In this instance, the LED is positioned near the right side, i.e., to the back, of the LED tunnel.

Figure 12:
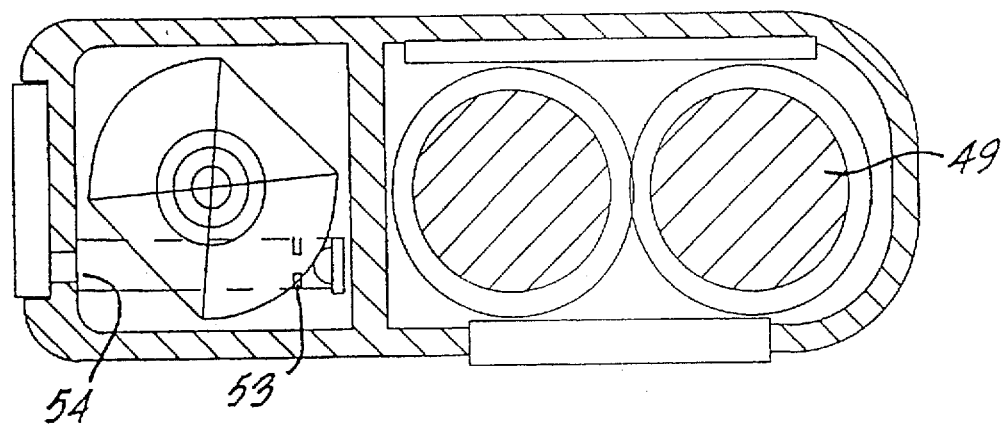
FIG. 12 is a section view taken along line 12—12 of FIG. 7 depicting a preferred embodiment of an LED arrangement.
Figure 13:
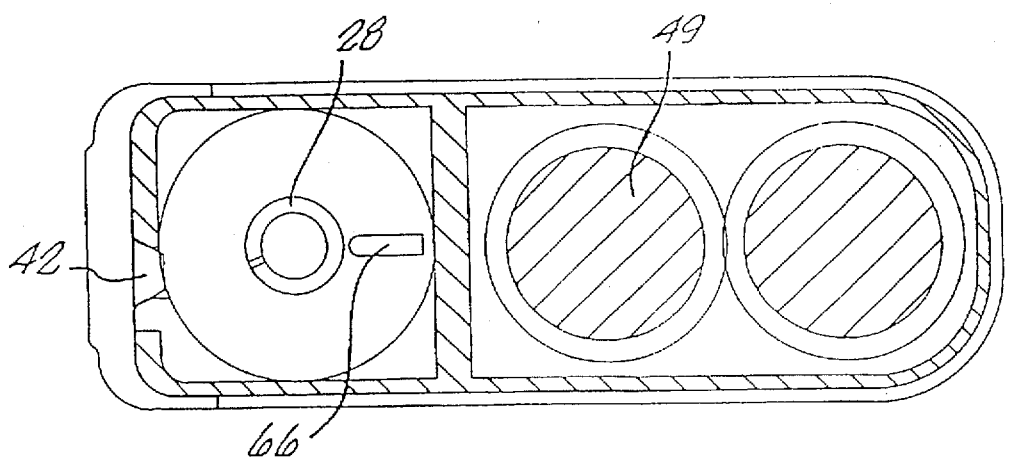
FIG. 13 is a section view taken along line 13—13 of FIG. 7.

Additionally, for precise collimation as may be needed for ocular uses, two apertures/baffles within the LED tunnel may be used. As shown in FIGS. 12, 24 and 32, the first aperture 53 serves to shape the light emitted by the LED and is preferably located directly adjacent to the LED. The second aperture 54 is preferably located at the opposite end of the tunnel closest to the LED port to serve to "aim" the LED beam and allow it to be observed only from the correct angle which corresponds to the mist beam.

Figure 29:
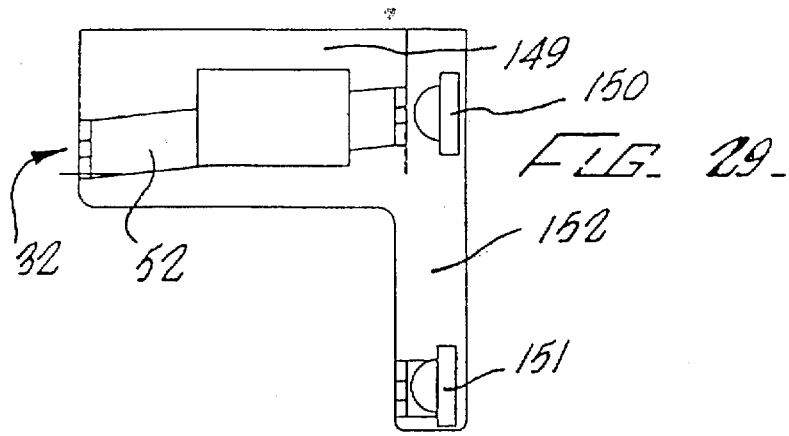
FIG. 29 is a side elevation view of an alternative optical spacer block in the embodiment of FIG. 28.

For administration of ocular drugs for which the most precise aiming is needed, an alternative embodiment uses two LEDs, as shown in FIGS. 28 and 29. The first LED 150 is located in an optical spacer block 149 at an identical location as in the embodiment of FIG. 9. For maximum aiming accuracy, a second LED 151 is provided within a downward extension 152 of the optical spacer block 149 and is located behind and slightly offset from the rotor so that the LED 151 is visible when the user's eye is located in direct line with the mist port. The LED 151 is offset from the rotor spin axis by the same degree as the mist port, since the mist droplets are emitted tangentially from the outer edge of the rotor. This offset (for a rotor spinning clockwise when viewed from above) is shown in FIGS. 4, 6 and 31. Upon actuating the on-off button, both LEDs are illuminated and the device is properly aimed only when both LEDs are simultaneously visible. In effect, the LED 151 behind the rotor defines the correct linear axis of the mist beam while the second LED 150 located above the mist port defines the correct distance by its beam's "intersection" with the first beam. The intersection of the two beams defines the correct distance and position of the device in space relative to the user's eye.

In an alternate design, a light pipe 47 shown in phantom in FIG. 11, formed of transparent molded plastic or fiber optics extends from the LED 31 to the LED port 32 and is used to guide the LED beam.

As best shown in FIGS. 7 and 8, the pump module 3 has a pump module housing 60. A nebulizing bowl 65 is formed at the front top section of the pump module housing 60. An anti-vortex baffle 66 (FIGS. 7, 22 and 23) extends partway into the nebulizing bowl 65 and prevents the rapidly spinning mist rotor 28 from causing the liquid to form a vortex which would reduce pumping efficiency and mist production. A bowl supply port 73 leads from the nebulizing bowl 65 into the pump module housing. A bracket 57 supports the pump module within the cartridge module (FIG. 30).

Referring to FIGS. 7 and 30, with the pump module 3 assembled to the nebulizing module 4, the upper mist chamber 29 and the nebulizing bowl 65 form a substantially enclosed mist chamber 50. Alternatively, the mist chamber 50 can be formed within an integral component.

As shown in FIGS. 7 and 8, within the pump module housing, an upper check valve 70 and a lower check valve 69 are provided above and below a diaphragm 72. The positions of the check valves in these figures correspond to the positions attained when the pump diaphragm is being depressed and liquid is flowing from the cartridge module into the pump module and from the pump module into the nebulizing bowl. A finger actuated pump button 67 slidably positioned within the pump module housing 60 overlies the diaphragm 72. An input nozzle 75 extends from the lower check valve downwardly into a bag neck 85 on a flexible plastic bag 84 in the cartridge module containing a liquid medium. The upper check valve 70 output connects with the bowl supply port 73 and prevents any reverse flow from the bowl 65 into the pump or cartridge. Both check valves allow flow only from the plastic bag 84 to the bowl supply port 73. The one-way liquid flow out of the pump and cartridge allows their liquid contents to remain free of potential contamination. Alternatively, the cartridge module housing itself may hold the liquid and no bag is used.

Referring to FIGS. 14–16, one or more keys 92 are optionally provided on the cartridge module housing to allow it to be assembled only to a nebulizing module having corresponding key slots 93. The keys and slots can be used to automatically select only appropriate cartridges for operation with a particular nebulizing module. For example, a nebulizing module designed to dispense eye comfort liquids would mechanically fit onto and accept only eye comfort cartridges and would not accept ocular drug or other cartridge types. Switches in the slots 93 are preferably electrically connected to the control and communication circuit to enable it to sense the insertion of a particular type of cartridge (e.g., anti-glaucoma drug) which can then instruct the user via the alpha numeric display how to self-administer the drug (e.g. "One spray per eye twice per day"). The key and key slot system, in conjunction with the control and communication circuit, can also be used to reset an alarm or to sense when a cleaning cartridge has been used according to the appropriate schedule. Through binary coding, use of only a few keys can provide indications for many different cartridges. For example, with three keys, as shown in FIG. 14, up to 8 different cartridges can be identified.

Turning to FIG. 34, preferably, the mist rotor 28 has a stem 120 flaring outwardly into straight cylindrical outer walls 122. An inner rotor chamber 121 has walls which taper conically outwardly from the bottom of the rotor to the top of the rotor. At the top of the chamber 121 is one or more mist holes 128 extending through the wall 122. The preferred diameter at the top of the chamber 121 is approximately from 3 to 10 mm. The distance D3 from the bottom of the rotor 28 to the mist hole 128 is preferably 5 to 20 mm. A scoop 125 having a knife edge is provided at the bottom of the rotor 28 in order to efficiently spin liquid into the rotor interior and preferably forms an angle C to the horizontal equal to angle B minus 10–20 degrees. The distance D1 separating the scoop 125 from the bottom edges 124 of the rotor 28 is preferably 2 to 4 mm. Of course, in each instance, other dimensions are possible.

Referring still to FIG. 34, the greater the angle A, the greater will be the volume pumped by the rotor 28 per unit time. In addition, the volume pumped by the rotor will increase with rotor speed, or with increased number or size of mist holes 128. The angle B at the bottom of the rotor 28, preferably ranges from about 35–60°, and most preferably about 45°. Angle B acts to create a fluid vortex in the rotor chamber 121 near the opening 126 which causes liquid to efficiently move via centrifugal forces from the opening 126 into the rotor chamber 121. Within the chamber 121, the fluid medium seeks its own level under centrifugal forces.

The preferred range of angle A is 0.5 to 1.5 degrees. A small angle is preferred for use with low viscosity spray mediums. A 0° degree angle for angle A, i.e. straight walls, also works but is less efficient as a pump. Larger angles, e.g., 1.5 to 10° degrees or more, for angle A, have a higher pump rate, and may be desired for more viscous mediums. A negative angle A, i.e. a conical chamber wider at the bottom than at the top, could also work if a liquid lifting mechanism is provided, e.g. an Archimedes screw.

The angled rotor bottom, defined by angle C, helps to pick-up small drops remaining in the nebulizing bowl 65 when the medium or the liquid level is low. With angle B at 0 degrees, the rotor also works but is less efficient as a pump and in picking-up drops.

The larger the angle C, the better small drops are picked-up by the rotor 28. The angle C should be as close to angle B as possible without making the knife edge and bottom of the rotor too thin and fragile. As angle C approaches 0 degrees, the rotor bottom becomes flatter and tends to spray liquid away from the opening 126, thus reducing the efficiency of small drop pick-up. With angle C at 0 degrees, the rotor operates, but the ability to pick-up small drops is greatly reduced.

The scoop 125, as shown in FIGS. 25, 27, 33 and 34, although not essential, acts to break-up the surface of the liquid (due to surface tension) and agitates the liquid sufficiently that some liquid is forced into the chamber 121 as the rotor starts to spin. The scoop also greatly increases the start-up reliability of the pumping process.

Figure 26:
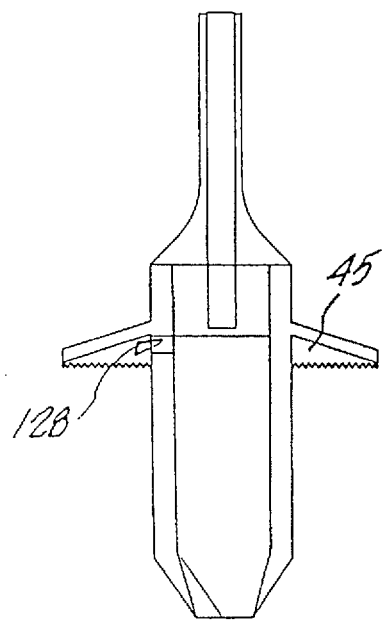
FIG. 26 is a section view of an alternate mist rotor embodiment.
Figure 25:
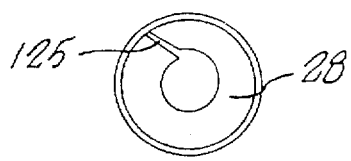
FIG. 25 is an end view thereof.
Figure 27:
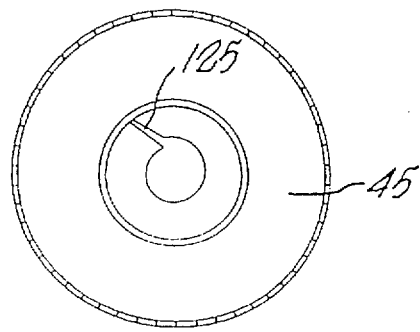
FIG. 27 is an end view thereof.

For certain liquids, it is desirable to further modify and break up the mist droplets produced by liquid exiting a mist hole 128 in order to produce an acceptably fine mist. To accomplish this, an alternative embodiment shown in FIGS. 26 and 27 adds a mist rotor barrier 45 around the hole 128 which flares downwardly below the hole 128. After liquid droplets exit the hole 128, they are further broken up as they travel along the lower surface of the mist rotor barrier 45 and impact on the rough outer edge of the barrier.

Figure 20:
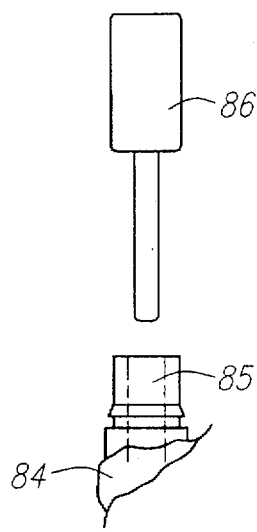
FIG. 20 is a right side elevation view fragment of the neck and plug of a bag for containing a liquid medium.

In use, a cartridge module 2 preferably includes a flexible plastic bag 84 containing a liquid medium. The bag is sealed with a removable plug 86, as shown in FIGS. 18 and 20. The flexible bag 84 eliminates the need for air intake, as atmospheric pressure induces collapse and emptying of the bag when the pump is activated. By preventing air from entering the plastic bag, the liquid medium can remain sterile, for drug and preservative free products. Accordingly, sprayed on products which are subject to oxidation are ideally delivered by the mist generator 1, since no externally derived oxygen or other atmospheric contaminants can enter the bag 84 during use and storage.

Figure 14B:
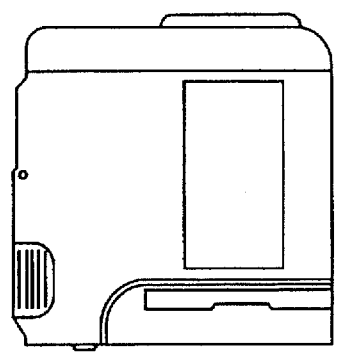
FIG. 14B is a right side elevation view of a nebulizing module.
Figure 15B:
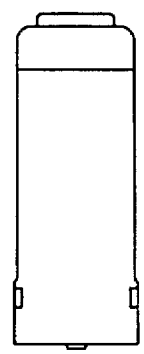
FIG. 15B is a rear elevation view of the nebulizing module of FIG. 14B.
Figure 14C:
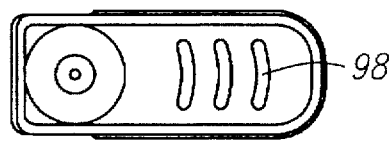
FIG. 14C is a plan-view of the pump module of FIG. 14A.
Figure 14A:
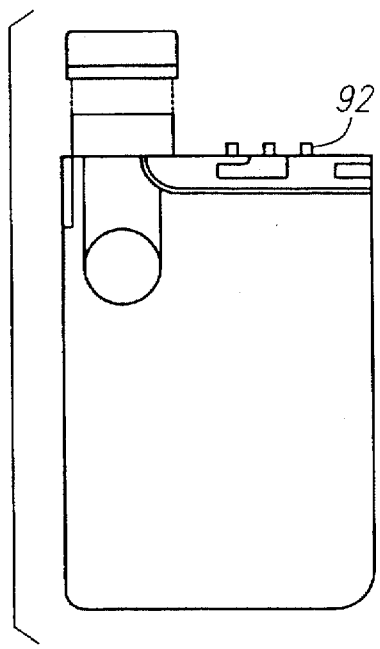
FIG. 14A is an exploded right side elevation view of a cartridge and pump module including a cap seal, and a keying arrangement for a nebulizing module.
Figure 15A:
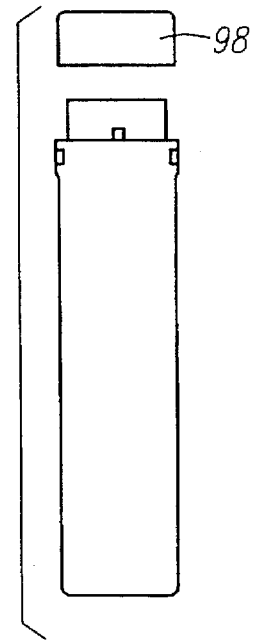
FIG. 15A is a rear elevation view of the cartridge and pump modules and cap seal of FIG. 14A.
Figure 21:
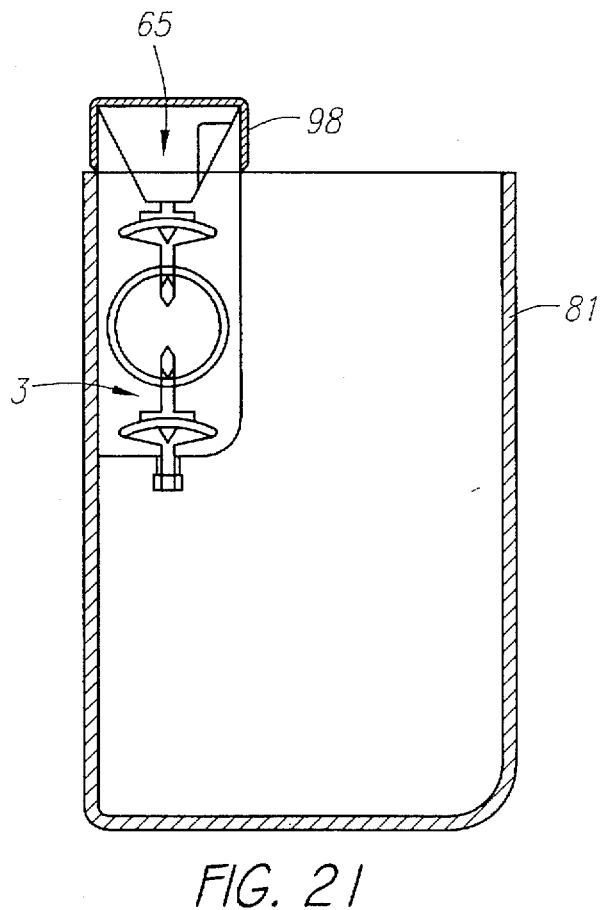
FIG. 21 is a side section view of a composite pump and cartridge module.
Figure 21A:
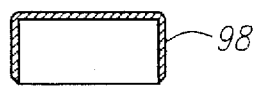
FIG. 21A is a section view of a removable cartridge seal.
Figure 22:
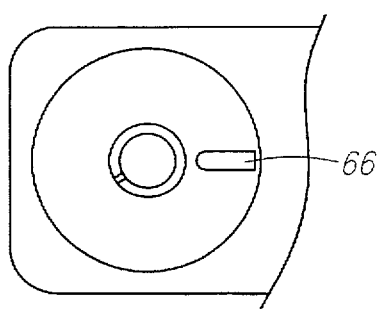
FIG. 22 is a plan view of a mist rotor and anti-vortex baffle.
Figure 23:
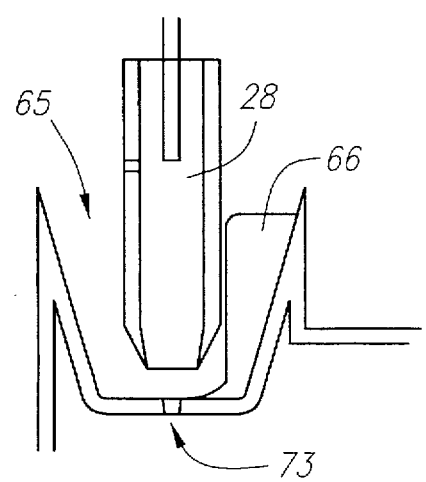
FIG. 23 is a right side elevation view fragment thereof.

As shown in FIGS. 16-19, two types of liquid-containing modules which attach to the nebulizing module are provided: (1) a composite module which contains both pump and cartridge components which are permanently fastened together during manufacture, and (2) non-composite pump and cartridge modules which are designed to allow the consumer to reuse the pump module with replacement cartridge modules. When the liquid in the composite module is used up, the entire composite module is intended to be discarded, preferably by recycling. By contrast, when the liquid in the non-composite, detachable pump and cartridge modules is used up, the pump module may be reused by attaching it to a new cartridge module. Alternatively, a partially used cartridge module may be separated from a connected pump module and re-sealed for storage by inserting plug 86 into the neck 85 of bag 84 in the cartridge module. Both composite and non-composite modules are provided with a removable cartridge seal 98 over the nebulizing bowl 65 as shown in FIGS. 14, 15 and 21.

As shown in FIGS. 7 and 8, the lower and upper check valves 69 and 70, respectively, and the diaphragm 72 form a pump 71. The pump 71 accurately delivers a defined amount of liquid from the cartridge and transfers it into the nebulizing bowl 65. Specifically, as the user depresses the pump button 67, the diaphragm 72 is compressed and expels a dose of liquid through the upper check valve 70 into the nebulizing bowl 65, through the bowl supply port 73. The lower check valve 69 and upper check valve 70 produce a uni-directional liquid flow from the cartridge module to the nebulizing bowl 65, without any backflow.

The volume of liquid delivered to the nebulizing bowl 65 by the pump 71 will vary. In ocular versions, each pump actuation will provide a sufficient amount of comfort liquid or drug to saturate the eye without overflowing—about one drop. With skin care products, by contrast, an increased amount of liquid will be delivered to facilitate mist delivery to a larger area of the skin. For products that require a specific volume of liquid to be delivered for each use (e.g., ocular or skin drugs), the volume of liquid delivered by the pump will be advantageously set at one dose of the substance.

The switch 23 on top of the nebulizing module is ergonomically placed at the natural resting position of the user's index finger, for both right and left handed users. As the switch 23 is rocked to the rear, the LED 31 illuminates generating a light beam which projects forward, for aiming purposes. For ocular versions, the light beam is visible only when the mist generator 1 is properly aimed to administer mist to the viewing eye. In skin care versions, or versions used to dispense lubricants, paints, solvents, surface protecting liquids, etc., a higher intensity beam is used to illuminate the area of skin on which the mist will be deposited. The LED may be any available color, especially red, yellow, amber or green. As the switch 23 is rocked forward, the motor 26 is energized and spins the rotor 28.

The rotor 28 is designed to function as a pump to draw liquid into the rotor chamber 121 and induce flow upwardly towards the mist hole 128. After the diaphragm pump is actuated, the bottom of the rotor 28 is immersed in the liquid medium contained within the nebulizing bowl 65. As the liquid enters into the bottom of the spinning rotor 28, the liquid accelerates and eventually spins along with the rotor 28. The conical taper of the cone chamber 121 continuously extends to a larger diameter, which, coupled with centrifugal force experienced by the liquid spinning with the rotor, causes the liquid to travel "downhill" on the inclined surface of the rotor and therefore upward towards the top of the rotor chamber 121. As the liquid is forced through the mist hole, mist droplets, of a defined size are formed, and are flung radially outwardly due to the centrifugal force of the spinning rotor. A fraction of the mist droplets exit through the mist port 33 as a focused uniform spray or beam of mist, suitable for a variety of medical, skin care, industrial and household uses. The mist beam travels directly from the rotor to the targeted surface.

The size and shape of the mist port can be varied to adjust the spray pattern. The mist port can be made adjustable with sliding closures or diaphragm like radially adjustable apertures. Multiple vertically spaced holes in the rotor combined with an elongated rectangular mist port may be used to provide a long narrow rectangular mist beam, for household, industrial or skin applications.

A shadow mask may be provided immediately behind the mist port, in the mist chamber, to shape the beam of mist and/or to stop any dripping on the outside of the mist port.

Mist droplets that impact the interior of the rotor mist chamber 50 flow downwardly to the bottom of the rotor mist chamber back into the nebulizing bowl 65 and are recirculated by the pumping action of the rotor 28. The number and size of the mist holes 128 can be varied, depending on the viscosity of the liquid used and the desired mist qualities.

For ocular comfort mist and ocular drugs, the mist will be very fine and a low volume. In contrast, an ocular first-aid product will produce a much larger quantity of coarser mist, so that the eye can be rapidly flushed of foreign bodies or chemical contaminants. Cosmetics and skin first-aid will also advantageously have a higher rate of mist in order to effectively cover the skin in several seconds. For delivery of fragrance products, a very small quantity of fine mist, similar to an ocular mist, is desirable.

The mist generator 1 can dispense different types of products by exchanging cartridge modules 2. A consumer may, for example, remove a skin moisturizing cartridge, re-seal it with the cartridge seal 98, and replace it with a sunscreen cartridge. Since virtually all residual liquid from the first cartridge is automatically removed from the nebulizing bowl during use, mixing of products is negligible.

For many skin care products, the mist generator 1 will use a rotor 28 selected to produce a mist similar in quality to a fog. Within several seconds, the mist will form a thin liquid layer. In such embodiment, the consumer will experience little or no sensation of mist impact on the skin which will be particularly advantageous for application of products like antiseptics, burn medications or local anesthetics to abraded, burned or otherwise delicate or sensitive skin. Similarly, many other products for skin care may be advantageously applied which include sunscreens or other skin-protective liquids, moisturizers, cosmetics, fragrances, insect repellents, anti-acne medications, antimicrobial substances, products for therapy of skin diseases, lipsome-based products or any other product useful for skin care which can be dispensed as a mist. For industrial or hobby use, lubricants, thinners, paints, solvents, surface-protective products, etc. can be applied, without the use of volatile organic compounds or propellants while avoiding the risk of spills, dripping, splashing, running or impacting on non-intended areas. Of course, for personal, industrial or hobby use, virtually any liquid can be applied by the mist generator. Of course, the outside shape and size of the mist generator may vary with its intended applications. For example, for household and individual uses, the cartridge module may be large and/or handle-shaped.

For delivery of a medium to the eye, the mist generator has several advantages over droppers. The LED allows the user to determine when the mist port 33 is properly aligned. Thus, the dose can be reliably applied to the eye in a uniform distribution, without any appreciable impact. Risk of injury to the eye is avoided as no pointed eyedropper tip is used. The mist generator 1 is accordingly is also advantageous for applying eye drop liquids or medications to children and for use by others with limited eye-hand coordination.

The control and communication circuit 25 may include a processor, memory and clock, depending upon the application. Optionally, the control and communication circuit 25 can be programmed to communicate to the user via the alpha numeric display 34 or the sound transducer 46, that the mist generator 1 has been used sufficiently to require cleaning with the cleaning module 95. For dispensation of certain products, for example ocular drugs, it may be particularly advantageous to program the control and communication circuit to operate the motor for a minimum time after the motor is actuated to assure that all of the drug in the nebulizing bowl is dispensed. Other functions that the control and communication circuit may optionally provide through the alpha numeric display 34 and/or sound transducer 46 are: remaining battery power; when to administer a product (or an alarm); dosing instructions; recording number and timing of uses for a daily log, or displaying other messages. Additionally, the control and communication circuit may allow the user to vary the speed of the motor.

The control and communication circuit 25 can also be programmed to prevent actuation of the mist generator 1, unless the cleaning cartridge 95 is used according to a particular schedule. Optionally, the cartridge keying system can provide an indication to the control and communication circuit 25 that the cleaning and disinfecting cartridge 95 has been inserted, with the control and communication circuit 25 programmed to operate the motor for a preset period of time to assure an adequate cleaning.

Thus, the control and communication circuit 25 can provide suggestions and reminders to the user, and can also disable the mist generator 1 unless and until a user follows specific instructions.

A daily use log, as recorded in the memory of the control and communication circuit 25, can be used by a health care provider to monitor the patient's compliance with prescribing instructions. Compliance monitoring can greatly aid in the conduct of clinical trials of experimental drugs and can help health care providers optimize drug administration. For this use, the control and communication circuit may additionally have an electronic interface to allow the connection of an external device which can read the data stored in the memory of the control and communication circuit.

For visually impaired users, voice synthesis may be included in the control and communication circuit 25 to provide verbal instructions, via the sound transducer 46. The sound transducer 46 can also act as an alarm, e.g., to remind users when to reapply a sunscreen at the beach. The control and communication circuit 25 may also be programmed to provide music or sound effects, for use with children or young adults.

In an alternative embodiment without a control and communication circuit, a mechanical or electrical timer is used to automatically run the motor for a pre-set time (e.g. 4–5 seconds), to insure all liquid in the nebulizing bowl is emptied. This reduces the likelihood of microorganisms growing in residual liquid left by the user due to insufficiently long running of the motor.

As shown in FIGS. 43–46, a dual medium cartridge 100 has a selection switch 105 on its back surface. First and second bags 103 and 104 are provided within the dual chamber cartridge 100. The first bag 103 has a delivery hose 109 passing through a hose collar 111 leading to a Y-branch 112. A slide pincher 107 attached to the switch 105 pinches off the delivery hose 109. On the opposite side of the cartridge 100 is a symmetrical arrangement with bag 104 having a delivery hose 110 passing through a collar and leading to the Y-branch. As shown in FIG. 44, with the selection switch 105 in position A, the pincher 107 pinches off the delivery hose 109, while delivery hose 110 remains open. As shown in FIG. 45, with the selection switch 105 in position B, the slide pincher 107 pinches off delivery hose 110, while delivery hose 109 remains open. As shown in FIG. 46, the selection switch 105 in position C is centered and both delivery hoses 109 and 110 are open so that contents of both bags 103 and 104 can be pumped out and mixed together.

The embodiment of FIGS. 43–46 may be especially useful when two products are commonly used in conjunction with one another. For example, a skier in a cold, dry environment may desire to apply a moisturizer to prevent skin chapping, followed by a sunscreen. Similarly, a hiker or sports enthusiast may apply a biting insect repellent followed by an anti-itch local anesthetic for areas already bitten or may apply a sunscreen and an anti-pain local anesthetic to already sunburned skin using the embodiments of FIGS. 43–46.

The embodiment of FIGS. 43–46 may also be particularly useful to administer a mixture of two substances which together are chemically unstable but when apart are relatively stable. For example, many drugs intended for ophthalmic administration are very soluble and relatively chemical stable at acidic pH (e.g., PH=2 to 6), but are relatively insoluble and unstable at the neutral pH of tears (pH=7.4). The eye is, however, very sensitive to irritation by acidic solutions and substantially acidic solutions cannot be used. One study, for example, found that 99% of people tested reported that ocular solutions with a pH of 5.8 were irritating (Deardorff, D. L., 1980, "Ophthalmic Preparations." Remington's Pharmaceutical Sciences, Eds. A Osol, et al. Easton, Pa.: Mack Publishing Company, 1504–1506). For this reason, many ophthalmic drugs are formulated at approximately neutral pH which does not produce irritation but which reduces the stability and shelf-life of the drugs.

The dual medium cartridge can be used to substantially solve this problem. In one bag, an ophthalmic drug is contained at an optimum acidic pH to increase stability and solubility. The other bag contains a neutral pH buffer. For this use, the design shown in FIGS. 43–46 is modified so that the selector switch is fixed to allow both bags to be simultaneously emptied by the pump at a mixing ratio which can be determined and fixed during manufacture. By actuating the pump, liquid from both bags is mixed in the pump and nebulizing bowl which results in the buffer changing the pH of the combined solution to a non-irritating neutral pH. Upon activating the motor, the spinning action of the rotor further ensures complete mixing of the solution for optimum comfort and safety.

A similar technique may be used to stabilize or otherwise modify compounds, which are stable under "non-physiological" chemical conditions, but which may be converted to a form that is physiologically acceptable by the addition of a second chemical solution contained in the second bag.

Similarly, this technique may be used to dispense any two liquids for which it is advantageous to store two components separately and combine them at the time of dispensation.

It should be noted that the second bag which contains the "modifying solution" may have a different size from the first bag (e.g., it may be much smaller in the case of a buffer.) This embodiment is also useful in industrial and hobby applications. For example, the mist generator 1 can be used as an air brush with different color paints provided in bags 103 and 104.

A composite cleaning and disinfectant module 95, as shown in FIGS. 35–42 is attachable to the nebulizing module 4, in the same manner as a cartridge module 2. A disinfecting liquid medium contained within the cleaning module 95 is pumped into the mist chamber 50, as is any other medium. A particularly preferred disinfecting liquid is an aqueous solution of hydrogen peroxide (e.g., 3% hydrogen peroxide) since it is an effective disinfectant and decomposes into water and oxygen and thus leaves no residue. When hydrogen peroxide is used as a disinfectant, it may be desirable to have a catalyst incorporated into the nebulizing bowl 65 to insure that all hydrogen peroxide is fully decomposed to water and oxygen after the cleaning process is completed. To accomplish this, a hydrogen-peroxide decomposing catalyst or enzymatic insert 140 is inserted into the nebulizing bowl which is immersed in the hydrogen peroxide disinfecting solution, as described in U.S. Pat. No. 3,912,451 incorporated herein by reference. A particularly preferred catalyst is platinum black which is coated in a thin layer on a solid plastic support. After the cleaning process is completed, the disinfecting solution is left to remain in the nebulizing bowl for a period of time sufficient to insure that the hydrogen peroxide is fully decomposed into water and oxygen. The spinning rotor sprays the disinfecting medium to clean the interior of the rotor 28 and the mist chamber 50. The safety shield 96 built into the cleaning and disinfecting cartridge 95 prevents the escape of any mist or liquid during cleaning, even if the mist port is inadvertently left open, to prevent the possibility of the user inadvertently spraying the disinfecting medium. After cleaning, the cartridge 95 is removed from the nebulizing module and the remaining cleaning liquid poured out.

The construction of the check valves is shown in FIGS. 47–51. As shown in FIGS. 47 and 48, a molded silicone rubber valve element 160 has a generally curved rectangular base 161 and a centered conical stopper 162. The base, by its shape, provides its own spring action. FIG. 49 shows the valve element 160 as installed in a valve housing 163, in the closed position. Under pressure, the valve element bows upwardly unsealing the stopper from the supply line 164. Liquid can then flow past the valve element into the delivery line 165. When pressure is removed, the spring force in the deformed base returns the stopper into the supply line 164. If pressure is created in the delivery line 165, the stopper is pushed with even additional force into the supply line 164, to prevent back flow. This design is exceptionally compact and produces accurate and consistent fluid delivery, without backflow. Metal components, e.g., springs, which can result in corrosion and contamination due to ion transfer and similar reactions, are avoided. Various elastomeric plastics may be used for the valve depending on their compatibility with the pumped medium.

In another preferred embodiment 170, as shown in FIGS. 51, 52, and 53 an alternative cartridge module 172 is configured to accept a standard medication bottle 174, typically having a volume of up to 15 ml, although larger volumes are possible. As shown in FIG. 52, a nebulizing module 171 attaches to the cartridge module 172 via retainer clip 173. More specifically, as shown in FIGS. 53 and 59, the retainer clip 173 holds a frame 176 of the cartridge module 172 to the nebulizing module 171. A bottle holder 178 is pivotally attached to the frame 176. A tab 175 on the retainer clip 173 engages a step 177 on the bottle holder 178 to hold it closed. Referring to FIGS. 59–62, a plug 182 is attached to a base 180 on the bottle holder 178. A fluid duct 184 connects an opening in the plug 182 to a supply line 186 leading to a pump 188, near the top of the frame 176. A biological air filter 190 which filters microbes, also supported on the frame 176, connects to the air inlet opening 194 in the plug 182 via an airline 192, and the check valve 191 before entering the bottle 174.

Referring to FIG. 62, the plug 182 has a central opening 194, into which the fluid outflow duct 184 and air inflow duct 185 connect. The air inflow duct 185 leads to the top of the plug opening 194, while the fluid outflow duct 184 begins at the bottom of the opening 194. A first locking diameter 196 on the plug 182 is sized to accept and seal against small neck bottles. Below the first locking diameter 196 is a larger second locking diameter 198 dimensioned to accept and seal larger neck bottles. Thus, the cartridge module 172 can accept two sizes of standard bottles. Other plug sizes can also be used to accommodate other bottle sizes. The plug 182 is substantially identical in shape to the shape of the factory eye dropper that is removed from the medication bottle before it is installed.

Figure 65:
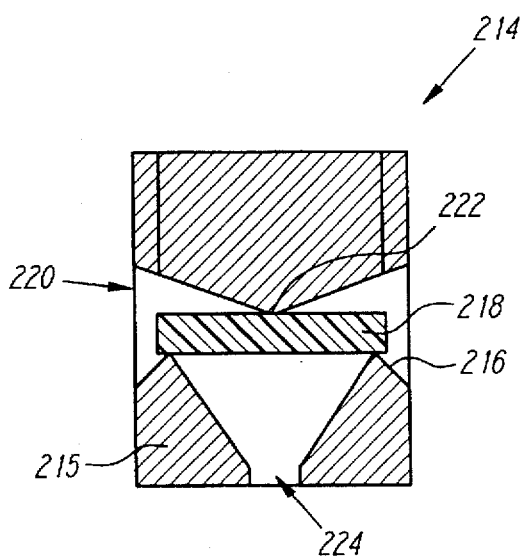
FIG. 65 is a section view fragment of an alternative outlet valve embodiment.
Figure 64:
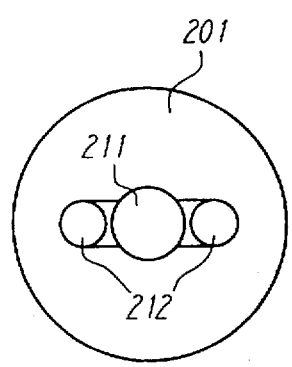
FIG. 64 is a plan view thereof.

Turning to FIGS. 64 and 65, an inlet valve 200 includes a valve body 201 having an annular valve seat 204. A valve cone 206 also supported by or part of the valve body 201 is spaced apart from the valve seat 204 to form a plenum 210 therebetween. A flexible disk 202, preferably of silicone rubber, is positioned between the valve seat 204 and valve cone 206. The spacing between the point on the valve cone 206 and valve seat 204 is less than the thickness of the rubber disk 202 (preferably approximately 0.030 inches). Accordingly, the point on the valve cone 206 pushes down on the center of the rubber disk 202, to preload the rubber disk 202 against the valve seat 204. Outlet ducts 212 extend to the valve body 201 to the plenum 210, and are joined to an outlet line 211 leading to the pump chamber. When the pump is activated, the reduced pressure on the inlet side causes the rubber disk 202 to bow or dish upwardly, thereby allowing fluid to flow through the inlet valve 200.

Figure 66:
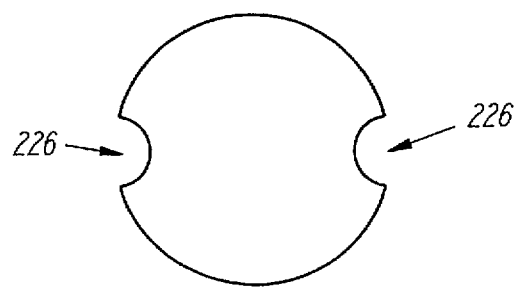
FIG. 66 is a plan view thereof.

Referring to FIGS. 65 and 66, an outlet valve 214 similarly includes a valve body 215 having a seat 216, cone 222 and flexible disk 218. Outlet ducts 226 are provided at the sides of the cone 222. An inlet 224 leads to the positive pressure side of the pump 188. When the pump 188 is actuated, the fluid pressure in the inlet 224 causes the rubber disk 218 to bow upwardly, allowing the inlet 224 to connect into the plenum 220 and to the outlet ducts 226.

Figure 67:
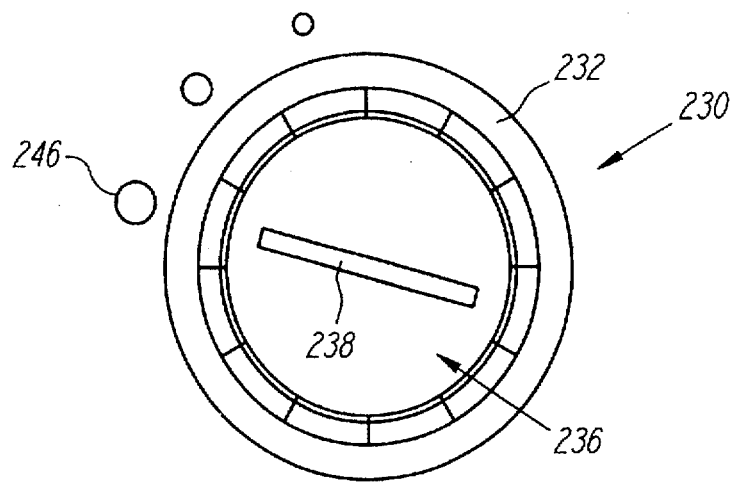
FIG. 67 is a plan view fragment of an adjustable pump button.
Figure 68:
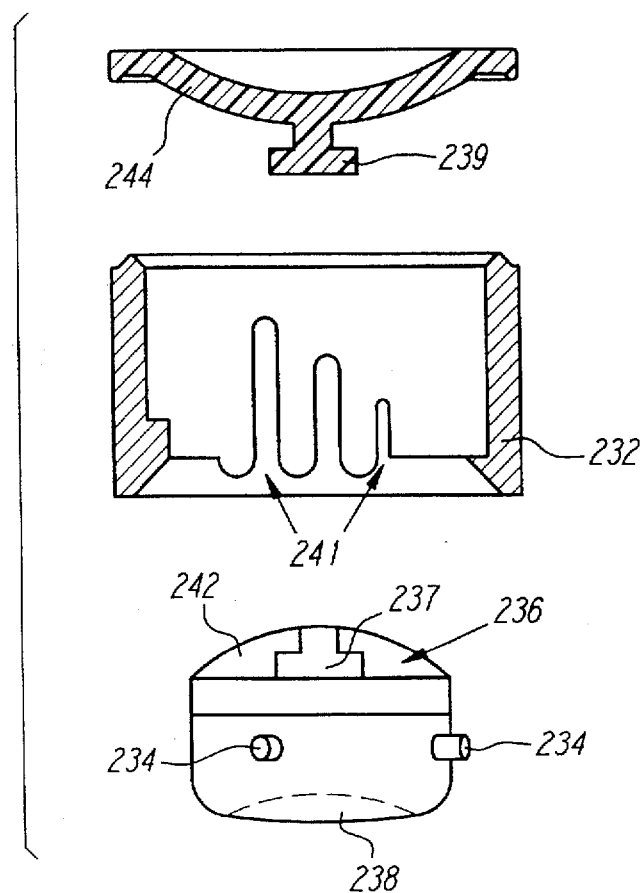
FIG. 68 is an exploded side elevation view in part section of pump components.

Turning now to FIGS. 67 and 68, an adjustable volume pump button assembly 230 has a button 236 including three projections 234 and a slot 238 in its outer surface. The inside surface 242 of the pump button 236 is generally spherical. A button housing 232 around the pump button 236 has detents or slots 241 corresponding to the 3 equally spaced apart pins or projections 234 on the button 236. FIG. 68 shows 1 of the 3 sets of slots which are equally spaced apart on the button housing 232. The button housing 232 is attached to the frame 176 of the cartridge module 172. The inside surface 242 of the pump button 236 presses against a diaphragm 244 in the pump 188. The pump button is attached to the center of the diaphragm via a slot 237 and a tab 239 which holds the pump button in position.

The user of the mist generator can adjust the volume of fluid pumped with each depression of the pump button 236 by turning the pump button 236 using e.g., a thumb nail or coin inserted into the slot 238. The button 236 is rotated over slots 241 to the desired position. Volume indicating marks 246 provided on the mist generator housing around the pump button allow the user to determine the volume setting of the adjustable pump button 230. The interaction of the projections 234 and slots 241 set the allowable travel of the pump button 236, and correspondingly adjust the volume pumped with each movement of the button. Preferably, three selectable volumes are provided.

Figure 54:
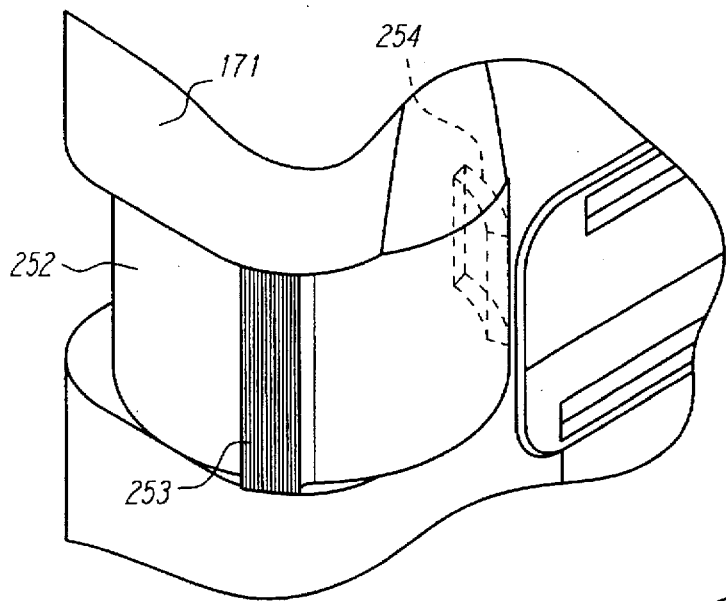
FIG. 54 is a perspective view fragment of the front of the device of FIG. 51 showing the mist port in the closed position.
Figure 54A:
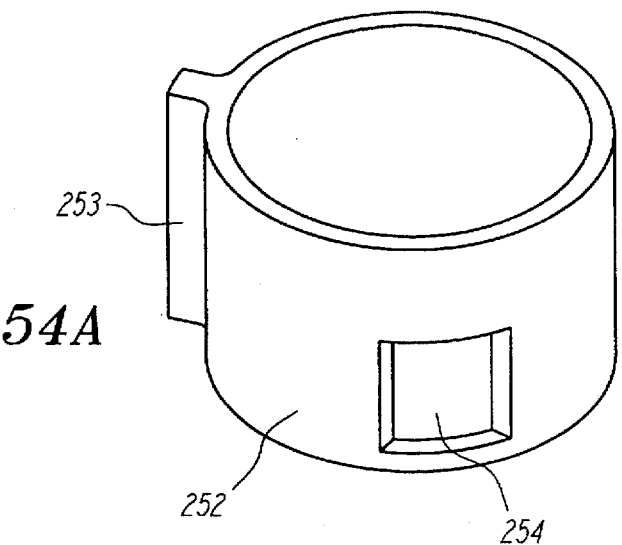
FIG. 54A is an enlarged perspective view-of the mist port cover shown in FIG. 54.
Figure 55:
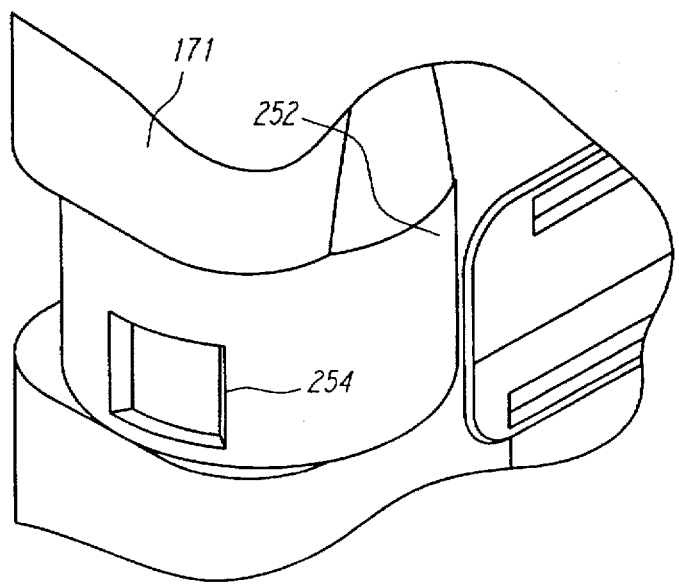
FIG. 55 is a perspective view fragment thereof showing the mist port in the open position.
Figures 56, 57:
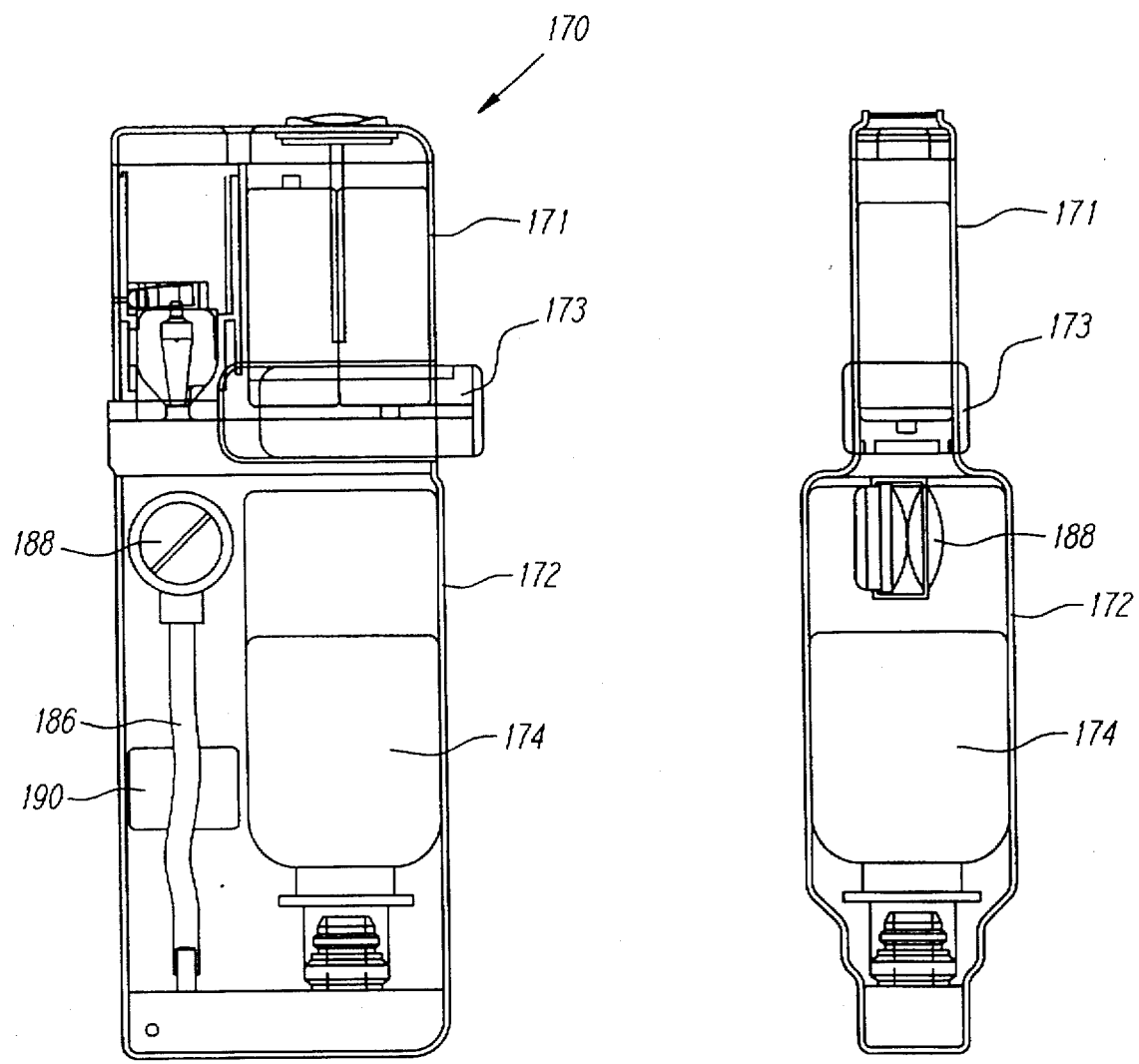
FIG. 56 is a partial section view taken along line 56—56 of FIG. 51.
FIG. 57 is a side elevation view thereof.
Figure 58:
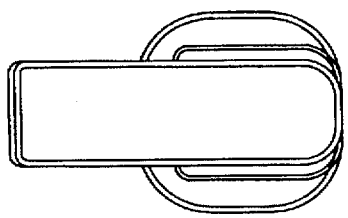
FIG. 58 is a bottom end view thereof.
Figure 59:
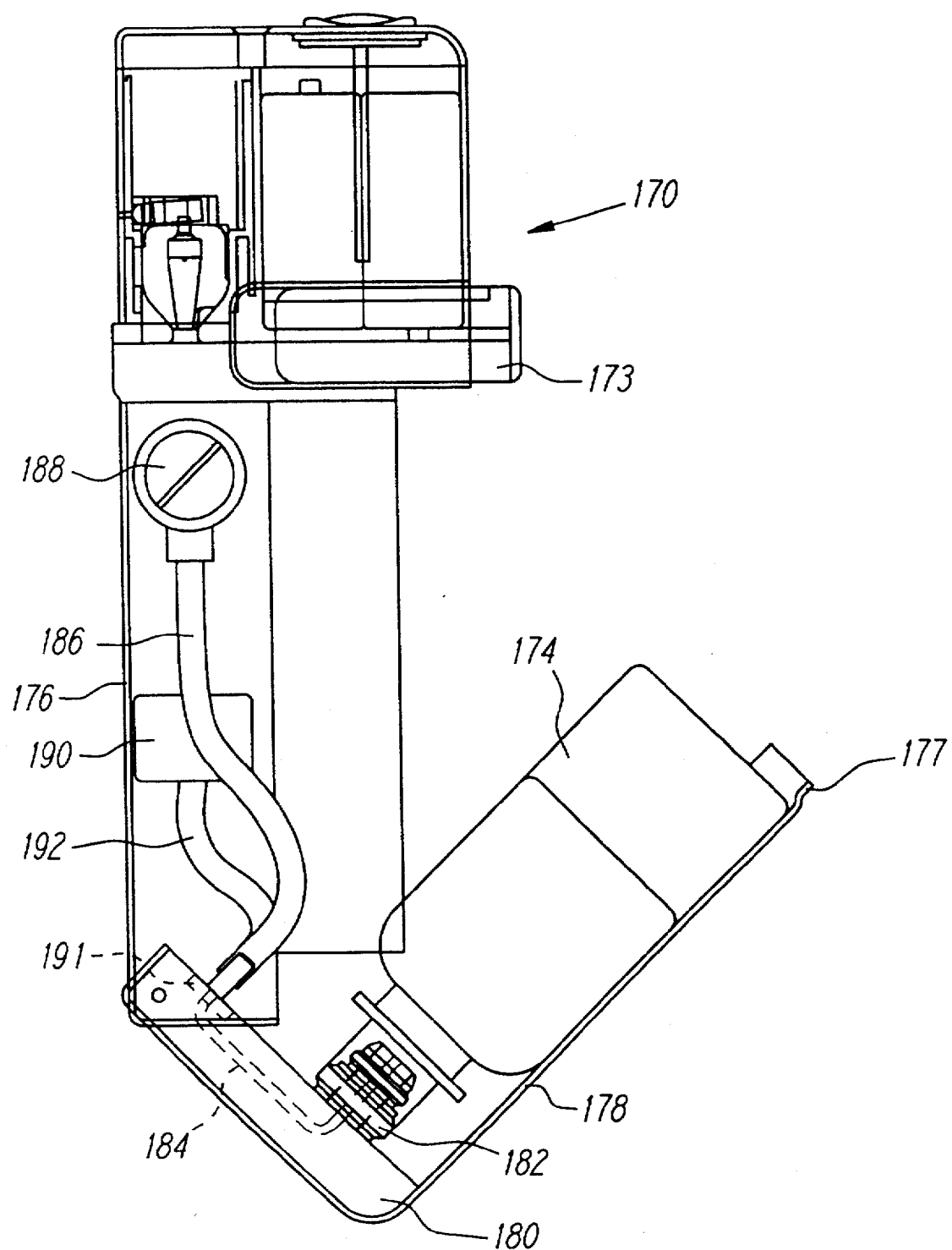
FIG. 59 is a side elevation view in part section of the embodiment of FIG. 51, showing the reservoir module in the open position.
Figure 60:
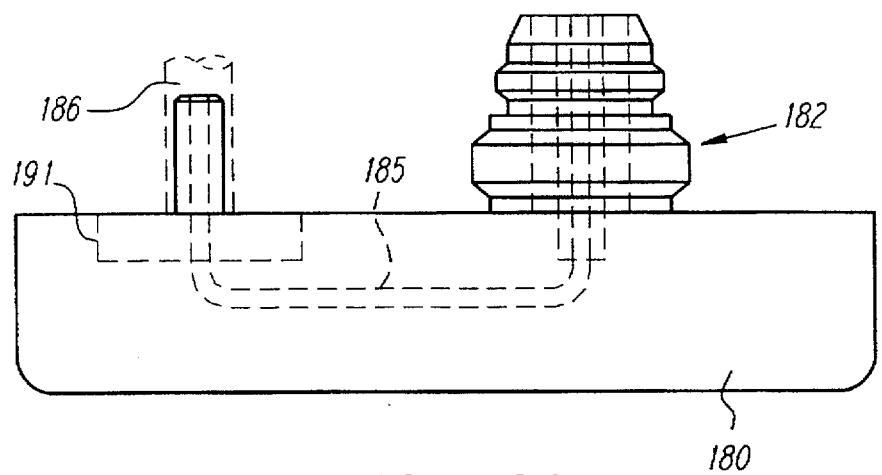
FIG. 60 is a side elevation view of the bottle holder of the reservoir module shown in FIGS. 53 and 59.
Figure 61:
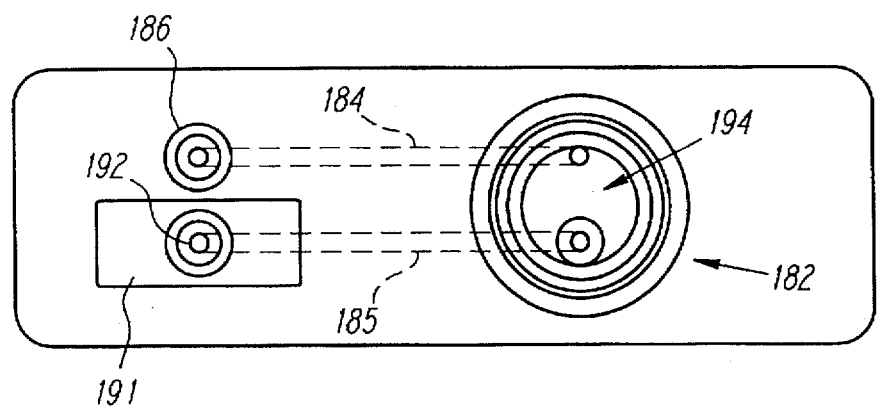
FIG. 61 is a plan view thereof.
Figure 62:
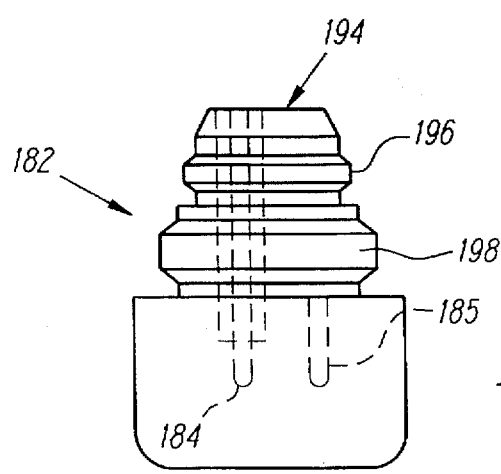
FIG. 62 is a right side elevation view thereof.
Figure 63:
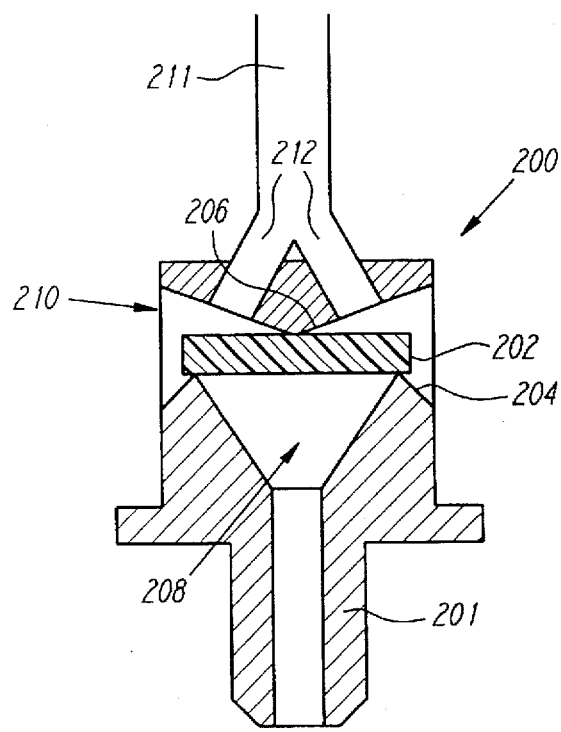
FIG. 63 is a section view fragment of an alternative inlet valve embodiment.
Figure 69:
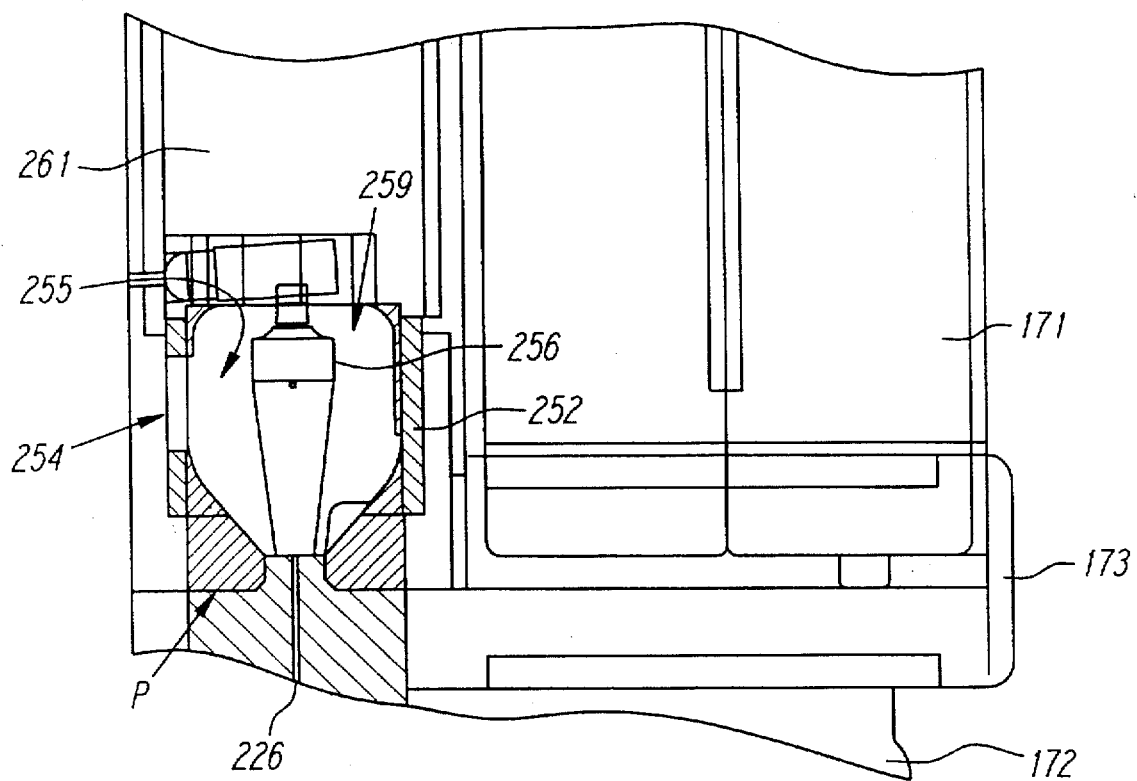
FIG. 69 is an enlarged side elevation view fragment in part section of the mist chamber of the embodiment of FIG. 51.

Referring to FIGS. 54, 55 and 69, a cylindrical mist chamber cover 252 is pivotally mounted on the nebulizing module 171. The mist chamber cover 252 has a single mist port 254, which may be square, rectangular, or of another shape, to adjust the mist spray pattern. The top and bottom cylindrical edges of the mist chamber cover 252 slidably seal against the nebulizing module. A finger tab 253 extends from the mist chamber cover 252 to facilitate rotation of the mist chamber cover 252 by finger actuation. With the mist chamber cover 252 moved into the "open" position shown in FIG. 55, the mist port 254 aligns with a window opening 255 on the nebulizing module housing, as shown in FIG. 69, allowing mist to spray out of the device 170. To prevent escape of mist or liquid (when the device 170 is not in use) (or is being cleaned), the mist chamber cover 252 is rotated e.g., 180 degrees, as shown in FIG. 54 so that the mist port 254 no longer aligns with the window 255, thereby substantially sealing the mist chamber. Contaminants are therefore largely excluded from the mist chamber during storage.

As shown in FIG. 69, the mist chamber 259 is preferably formed by an interference fit of the nebulizing module 171 over a cartridge module, e.g., 172. With the motor and mist rotor installed from the top of the mist chamber 259, the orientation of the separation line P between the modules helps to avoid having droplets form and adhere to the mist chamber walls at the conical-cylindrical transition shown e.g., in FIG. 7.

The mist rotor 256 as shown FIGS. 70–73 preferably tapers to larger diameters, and thicker walls, from bottom to top. The mist rotor 256 has a scoop 257 at its lower end, to help draw fluid into the cone. Referring to FIG. 70, the mist rotor 256 preferably has a lower outside diameter I of approximately 0.088", a height F of 0.470", and a mist hole H having a diameter of approximately 0.013", located at dimension G approximately 0.105" below the top surface of the mist rotor 256. The top outside diameter of the mist rotor E is preferably 0.187". Referring to FIG. 73, the lower inside diameter J is preferably 0.078" and diameter K is preferably 0.106". Of course, other dimensions may also be used.

Referring to FIGS. 53 and 59, to install a medication bottle 174, the bottle holder 178 is pivoted open by releasing the retainer clip 173. This allows the bottle holder 178 to pivot or swing out and away from the frame 176 by about 45°. The factory installed eye dropper is removed from the medication bottle 174. The mist generator 170 is turned upside down so that the plug 182 is facing down. The medication bottle 174 remains upright. The plug 182 is then pushed into the neck of the upright bottle 174. This installation can be accomplished by either a pharmacist or the user. The plug 182 on the bottle holder 178 is pressed into the neck of the bottle 174 until it is fully engaged and seals with a snapping action.

As fluid is pumped out of the bottle 174 via duct 184 to the pump 188, air enters the bottle to replace the volume of the fluid pumped out. The air passes through the biological filter 190 and through a check valve 191 before entering into the bottle 174 through the air line 192 and air inflow duct 185. The check valve 191 prevents fluid flowing into the filter 190. The filter 190 substantially prevents airborne contaminants from entering into the bottle 174. Operation of the other components of the device 170 is substantially as described above for the device of FIGS. 1–10.

The cartridge module 172 may be used in place of the cartridge module 2, to allow the user a choice of fluid reservoirs.

Thus, a novel mist generator is disclosed. While embodiments and applications of this invention have been shown and described, it would be apparent to those skilled in the art that many more modifications are possible without departing from the inventive concepts herein. The invention, therefore, is not to be restricted except in the spirit of the appended claims.

I claim:

1. A mist generator comprising:

a housing;

a mist rotor in the housing having at least one mist hole, rotatably supported substantially within a mist chamber;

a motor linked to the mist rotor;

a pump adjustable to deliver a varying volume of fluid with each actuation of the pump attached to the housing, and separate from the mist rotor for supplying a fluid medium to the mist rotor.

2. The mist generator of claim 1 wherein the housing is portable and handheld.

3. The mist generator of claim 2 further comprising a bowl supply port in the bowl.

4. The mist generator of claim 1 wherein the mist rotor has a conically tapering inner surface with the at least one mist hole extending through the rotor to the inner surface.

5. The mist generator of claim 1 further comprising an anti-vortex means in the mist chamber.

6. The mist generator of claim 1 further comprising a mist port attached to the housing for shaping a mist spray.

7. The mist generator of claim 1 further comprising a cartridge module attachable to the housing for holding mist medium.

8. The mist generator of claim 7 wherein the mist medium is a therapeutic fluid for use in the eye.

9. The mist generator of claim 7 wherein the mist medium is a non-therapeutic fluid for use in the eye.

10. The mist generator of claim 9 wherein the fluid is a member selected from the group consisting of saline solution, artificial tears, and rewetting solution.

11. The mist generator of claim 7 wherein the mist medium is a therapeutic fluid for use on the skin.

12. The mist generator of claim 7 wherein the mist medium is a non therapeutic fluid for use on the skin.

13. The mist generator of claim 7 wherein the mist medium is a fragrance.

14. The mist generator of claim 7 wherein the mist medium is a lubricant.

15. The mist generator of claim 7 wherein the mist medium is a surface treatment selected from the group consisting of paints, stains, dyes, inks, lacquers, urethanes, lubricants, and surface protective agents.

16. The mist generator of claim 7 further comprising a medication bottle in the cartridge module.

17. The mist generator of claim 1 wherein the mist rotor has a generally elongate tapered cylindrical shape.

18. The mist generator of claim 1 wherein the mist rotor has smooth and continuously uniform tapered interior cylindrical walls.

19. The mist sprayer of claim 1 further comprising an anti-vortex vane in the mist chamber.

20. A method of spraying a fluid mist comprising the steps of:

pumping fluid with a finger actuated pump to deliver a fluid to a mist chamber;

spinning a mist rotor having a mist hole within the mist chamber, thereby causing the fluid to be drawn up into the mist rotor;

forming fine mist fluid droplets within the mist chamber by passing fluid through the mist hole in the mist rotor under centrifugal force; and directing the mist of fluid droplets in the direction of an area to be sprayed.

21. The method of claim 20 wherein the fluid is a member selected from the group consisting of therapeutic and non-therapeutic eye or skin treatments, lubricants, and liquid surface treatments.

22. The method of claim 20 further comprising the step of shaping the mist.

23. The method of claim 20 further comprising the step of selecting a volume of fluid delivered to the mist chamber.

24. The method of claim 20 further comprising the step of directing a light source onto the area to be sprayed.

25. The method of claim 20 further comprising the step of selecting a spinning speed of the mist rotor.

26. The method of claim 20 further comprising the step of digitally recording the timing, duration, or occurrence of the pumping step or spinning step.

27. The method of claim 20 further comprising the step of annunciating an instruction or reminder.

* * * * *